United States Patent
Cai et al.

(10) Patent No.: US 6,342,210 B1
(45) Date of Patent: Jan. 29, 2002

(54) ANTIPERSPIRANT ACTIVES FROM A GLASS FORM AND PRODUCTS MADE THEREWITH

(75) Inventors: Heng Cai, Yardley, PA (US); Xiaozhong Tang; Aixing Fan, both of Bridgewater, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/839,659

(22) Filed: Apr. 20, 2001

(51) Int. Cl.⁷ .............................. A61K 7/32; A61K 7/34; A61K 7/38; A61K 7/00; A61K 31/74
(52) U.S. Cl. .......................... 424/65; 424/66; 424/68; 424/78.02; 424/78.08; 424/400; 424/401
(58) Field of Search .................. 424/65, 66, 68, 424/78.02, 78.08, 400, 401

(56) References Cited

U.S. PATENT DOCUMENTS

| | | |
|---|---|---|
| 4,359,456 A | 11/1982 | Gosling et al. |
| 4,775,528 A | 10/1988 | Callaghan et al. |
| 4,871,525 A | 10/1989 | Giovanniello et al. |
| 4,987,243 A | 1/1991 | Kawam et al. |
| 5,098,698 A | 3/1992 | Kawam et al. |
| 5,654,362 A | 8/1997 | Schulz, Jr. et al. |
| 5,725,836 A | 3/1998 | Rouanet et al. |
| 5,864,923 A | 2/1999 | Rouanet et al. |
| 5,997,850 A | 12/1999 | Tang et al. |

FOREIGN PATENT DOCUMENTS

| | | |
|---|---|---|
| EP | 0512770 | 11/1992 |
| EP | 0653203 | 5/1995 |
| EP | 0499456 | 12/1996 |
| WO | WO 9219221 | 4/1992 |

*Primary Examiner*—Shelley A. Dodson
(74) *Attorney, Agent, or Firm*—Rosemary M. Miano

(57) ABSTRACT

A method for forming micronized antiperspirant salts is disclosed wherein the method comprises the steps of: (1) forming an aqueous salt solution of a parent salt wherein the solution has a glycol content of less than 5 weight %; (2) pouring the salt solution onto a bounded flat surface; (3) evaporating the solvent from the salt solution so as to form a glass; (4) breaking up the glass using one or more steps to form particles having an average size in the range of 0.5–2.00 cm$^2$; (5) mixing the particles from step (4) with a non-aqueous liquid vehicle in which the salt is not appreciably soluble and subjecting the mixture to an intermediate grinding process to form a suspension with particles having an average size of less than 200 microns; and (6) grinding the mixture from step (5) at a temperature in the range of 20–70 degrees C. without added water or external heating being required so that the particles in the suspension have an average particle size of less than or equal to 20 microns.

34 Claims, No Drawings

US 6,342,210 B1

ANTIPERSPIRANT ACTIVES FROM A GLASS FORM AND PRODUCTS MADE THEREWITH

FIELD OF THE INVENTION

This invention relates to the formation of enhanced antiperspirant salts containing (1) aluminum or (2) aluminum and zirconium polymeric species, the salts themselves and cosmetic compositions formulated with such salts. In particular, the use of a glass-forming step for the antiperspirant active is useful in forming actives with lower refractive indices. This results in (1) a clearer final formulation, especially with a selected polyamide gelling agent; and (2) an ability to obtain suspension products which have the appearance of a clear gel without the wetness frequently associated with traditional gels.

BACKGROUND OF THE INVENTION

In an earlier and co-pending case assigned to the same assignee as this application, U.S. Ser. No. 9/597,322 filed Jun. 19, 2000, it was disclosed that certain grinding techniques which resulted in antiperspirant actives in a certain micron particle size range have shown improved efficacy in traditional screening tests. It has now been found that if an antiperspirant salt is first dissolved in water, made into a glass by evaporation of the water, and then subjected to the grinding process as described in that earlier case, an improved salt can be obtained with a surprising new property of a lower refractive index.

By way of general background, antiperspirant salts, such as aluminum chlorohydrex (also called aluminum chlorohydrex polymeric salts and abbreviated here as "ACH") and aluminum zirconium glycine salts (abbreviated here as "ZAG", "ZAG complexes" or "AZG"), are known to contain a variety of polymeric and oligomeric species with molecular weights (MW) ranging from 100–500,000. It has been clinically shown that, in general, the smaller the species, the higher the efficacy for reducing sweat.

In an attempt to increase the quality and quantity of smaller aluminum and/or zirconium species, a number of efforts have focused on (1) how to select the components of ACH and ZAG which affect the performance of these materials as antiperspirants and deodorants; and (2) how to manipulate these components to obtain and/or maintain the presence of smaller types of these components. These attempts have included the development of analytical techniques. Size exclusion chromatography ("SEC") or gel permeation chromatography ("GPC") are methods frequently used for obtaining information on polymer distribution in antiperspirant salt solutions. With appropriate chromatographic columns, at least five distinctive groups of polymer species can be detected in a ZAG, appearing in a chromatogram as peaks 1, 2, 3, 4 and a peak known as "5". Peak #1 is the larger Zr species (greater than the pore size of column materials, (particularly greater than 120–125 Angstroms). Peak 2 is the larger aluminum species (particularly greater than 120–125 Angstroms). Peak 3 is the medium species. Peak 4 is the smaller aluminum species (aluminum oligomers), and has been particularly correlated with enhanced efficacy for both ACH and ZAG salts. Peak 5 (sometimes referred to as Peak 5–6) is the smallest aluminum species. The retention time ("Kd") for each of these peaks varies depending on the experimental conditions. Various analytical approaches for characterizing the peaks of ACH and various types of ZAG actives are found in "Antiperspirant Actives-Enhanced Efficacy Aluminum-Zirconium-Glycine (AZG) Salts" by Dr. Allan H. Rosenberg (Cosmetics and Toiletries Worldwide, Fondots, D. C. ed., Hartfordshire, UK: Aston Publishing Group, 1993, pages 252, 254–256). Using GPC, Rosenberg describes four peaks identified as Al Kd 0.0; 0.24; 0.40; and 0.60. Activated ACH is identified as material having an enriched Al Kd 0.4 content. Spray drying AZG within a prescribed time frame to fix the desired distributions of the 4 peaks in a powder has also been suggested in the same reference Rosenberg, A., "New Antiperspirant Salt Technology" (*Cosmetics and Toiletries Worldwide,* Fondots, D. C. ed., Hartfordshire, UK: Aston Publishing Group, 1993, pages 214–218).

Other techniques have been developed as well such as size exclusion chromatography ("SEC") sometimes referred to as gel permeation chromatography ("GPC") (depending on the type of column used) which can utilize SEC columns in HPLC systems. A combination system combining inductively coupled plasma ("ICP") with SEC for an SEC-ICP system has also been developed. Such techniques can be used to investigate whether zirconium and aluminum species co-elute at similar retention times or elute separately from the column at different retention times. In a particular method the SEC and ICP equipment are linked to characterize and monitor the zirconium and aluminum content and species in an aqueous solution of zirconium and aluminum, especially ZAG solutions. This is useful to investigate whether zirconium and aluminum species co-elute at similar retention times or elute separately from the column at different retention times.

Attempts to activate antiperspirant salts with improved efficacy have included developing processes for obtaining better types of ACH such as by heating solutions of ACH with or without elevated pressure in order to depolymerize larger aluminum species into Peak 4 species. Examples can be found in U.S. Pat. No. 4,359,456 to Gosling et al. Since ACH solutions may be used as starting materials for aluminum zirconium glycine (ZAG or AZG) salts, heating ACH solutions has also been used to enrich Peak 4 oligomers before spray drying.

U.S. Pat. No. 4,775,528 to Callaghan et al describes the formation of a solid antiperspirant composition having an Al:Zr atomic ratio from 6:1 to 1:1; the GPC profile of the antiperspirant in solution gave a ratio of at least 2:1 for peak 4/peak 3. This reference specifies that the zirconyl hydrochloride be mixed with the aluminum chlorhydroxide solution before the drying step is completed.

U.S. Pat. No. 4,871,525 to Giovamuiello, et al. also teaches a method to activate ZAG by thermally enriching the Al Kd 0.4 content in aqueous solutions.

The dilution/heating process that is normally used to activate the aluminum species involves heating a dilute aqueous solution of the antiperspirant salt and then spray drying the material to a powder form. Aside from activity issues, the refractive indices of such salts are in the range of 1.49–1.52 for aluminum salts and in the range of 1.55–1–57 for aluminum zirconium salts which makes it difficult to obtain clear products with good skin feel at reasonable cost.

Further references include European patent Application 0 499 456 A2 assigned to Bristol-Myers Squibb Company describes a ZAG complex and a process for making the complex comprising mixing zirconium hydroxychloride, a selected aluminum chloro species and an amino acid in aqueous solution and, optionally drying the aqueous solution to obtain a dry ZAG salt.

European Patent Application EP 0 653 203 A1 to Rosenberg et al describes a process for making ZAG salt with high antiperspirant activity. According to this reference, glycine is added to Zr starting materials at ambient temperature, and the mixed Zr/glycine is admixed with the aluminum chlorohydrate starting material immediately prior to spray drying in a continuous or semi-continuous operation.

U.S. Pat. No. 4,871,525 to Giovanniello et al describes a solid powder of aluminum zirconium hydroxyl halide glycinate complex having improved antiperspirant activity wherein the glycine is used to prevent gel formation. The ratio of Zr to glycine is less than 1:1.

In general, it has been found that large or medium size aluminum polymeric species (Peak 2 and Peak 3 species) in antiperspirant salts can be converted to smaller ones (Peak 4) by diluting an aqueous solution of the salt to a concentration of about 2–20% (w/w), and heating the diluted solution to a temperature of about 90° C. for a period of time. (Peak 5 or Peak 5–6 has not usually been mentioned because chemical equilibrium factors in aqueous solutions have limited the ability to increase this peak.) However, there has been no thermal activation method available to convert large zirconium species into small ones. It has only been possible to prevent small zirconium species from polymerizing by forming complexes with amino acids or with salts thereof.

With regard to making smaller particle sized antiperspirant salts, reference is made to U.S. Pat. No. 5,098,698 to Kawam et al and U.S. Pat. No. 4,987,243 to Kawam et al both describe a process for preparing submicron antiperspirant adduct wherein the first step is dissolving a mixture of an aluminum-containing salt and a stearic stabilizer in a solvent. U.S. Pat. No. 5,864,923 to Rouanet et al and U.S. Pat. No. 5,725,836 teach the use of supercritical fluids to form aerogels.

Even if modification of current spray drying processes is used, spray drying a solution of antiperspirant salt immediately to remove water would result in an anhydrous powder with the same polymer distribution of aluminum and zirconium species in the solution. The finest powder commercially available has a particle size distribution from 2–10 microns with average size of about 7 microns as made by a dry-grinding method.

It has now been found that a process in which an antiperspirant salt is first dissolved in an aqueous environment and formed into a glass before grinding to small size particles as described below to activate the aluminum/zirconium salt, provides a superior antiperspirant active with respect to being able to form clear products. As in the previously described process for grinding the antiperspirant salt, the antiperspirant salt containing aluminum or aluminum and zirconium is activated by converting both large aluminum and zirconium polymers into small ones without the use of heating or dilution or the need for the special last minute addition of the zirconium component.

SUMMARY OF THE INVENTION

This invention comprises a method for forming micronized antiperspirant salts having a refractive index in the range of 1.42–1.49 (for example, 1.46) for aluminum salts and 1.46–1.52 (for example, 1.49) for Al—Zr salts comprising the steps of:
(1) forming an aqueous salt solution (preferably water) of a selected parent salt either by purchasing a solution of salt or making a solution with salt in a powder form wherein salt itself is selected from the group consisting of aluminum salts and aluminum zirconium salts and the glycol content of the salt solution is less than 5 weight %;
(2) pouring the salt solution onto a flat surface;
(3) evaporating the solvent from the solution so as to form a glass;
(4) breaking up the glass using one or more steps to form particles having an average size suitable for grinding (for example in the range of 0.5–2.00 $cm^2$);
(5) mixing the particles from step (4) with a non-aqueous liquid vehicle (for example, a non-aqueous and hydrophobic vehicle) in which the salt is suspended but not appreciably soluble (less than 1.0% soluble) and subjecting the mixture to an intermediate grinding step (for example, a homogenizing process) to form a suspension with particles having an average size in the range of 200–1000 microns or below (and particularly, a size of less than or equal to 200 microns); and
(6) grinding the mixture from step (5) at a temperature in the range of 20–70 degrees C. (particularly 40–70 degrees C. and, more particularly, 50–70 degrees C.) without added water or external heating using additional appropriate equipment so that the particles in the suspension have an average particle size of less than or equal to 20 microns (particularly less than or equal to 5–10 microns and, even more preferably, less than or equal to 1.5 microns).

It should be noted that, in general, the grinding steps form salts with comparable aluminum zirconium profiles as described in U.S. Ser. No. 9/597,322 listed above. The important difference, however, is the decrease in refractive indices that is achieved by use of the glass formation step. As in the previous case, the poorer performing parent salts will experience larger increases in smaller aluminum species and larger decreases in larger zirconium species.

The grinding process itself has previously been noted in the earlier case as forming a salt with the profile of an enhanced antiperspirant active. In addition to the difference in refractive indices, several important distinctions in the formulation of antiperspirant and/or deodorant compositions in this invention, however, must be noted:
(1) the final antiperspirant and/or deodorant products made in this invention will be anhydrous and will not contain any more than 5 weight % water (preferably less than 1%) in the vehicle, since the use of any added water in the formulation will reduce the ability to form clear products; and
(2) the final antiperspirant and/or deodorant products made in this invention will have a glycol level less than 5% (including glycols from any source in the formulation) since glycols appear to interfere with the formation of the glass.

In general, the translucent to clear antiperspirants and/or deodorants that comprise this invention will be made with the ground particles from the glass described above suspended in a non-aqueous base. The final product may be made in the form of sticks, soft solids, gels, creams, roll-ons, aerosols, or sprays.

DETAILED DESCRIPTION OF THE INVENTION

This invention comprises forming glasses with solutions of antiperspirant salts, and grinding the glass down to micronized form to activate the glass and form micronized active salts that have lower refractive indices. These micronized salts are added to base materials to form translucent to clear suspension antiperspirant and/or deodorant products. The activity of the aluminum or the aluminum/zirconium salt is evaluated on the basis of the distribution of various peaks for small and large Al and Zr species. A profile with information on peak distribution may be obtained using SEC techniques such as those described in U.S. Ser. No. 9/597, 322. An aluminum or aluminum /zirconium salt is described as having a composition wherein the amount of smaller aluminum species as represented by Peak 4+Peak 5 is increased by an amount of at least 10% (particularly by an amount of at least 20% and, even more particularly, by an amount of at least 25%) over the parent salt; and, if zirconium is present, the area of Peak 1 in the parent salt, i.e. before grinding, is at least 10% greater (particularly 20% greater and, more particularly, 25% greater) than the area of Peak 1 after grinding.

The parent salt may be selected from a variety of aluminum and aluminum-zirconium antiperspirant active salts. These salts include all those which are commonly considered antiperspirant active materials and covered by FDA Monograph as Category I antiperspirant actives and which contain aluminum or aluminum and zirconium. Examples of suitable salts that can be used as starting materials include conventional aluminum and aluminum/zirconium salts, as well as aluminum/zirconium salts complexed with a neutral amino acid such as glycine, as known in the art. See each of European Patent Application Number. 512,770 A1 and PCT case WO 92/19221, the contents of each of which are incorporated herein by reference in their entirety, for disclosure of antiperspirant active materials.

Suitable materials include (but are not limited to) aluminum chlorides (various types including, for example, anhydrous form, hydrated form, etc.), zirconyl hydroxychlorides, zirconyl oxychlorides, basic aluminum chlorides, basic aluminum chlorides combined with zirconyl oxychlorides and hydroxychlorides, and organic complexes of each of basic aluminum chlorides with or without zirconyl oxychlorides and hydroxychlorides and mixtures of any of the foregoing. These include, by way of example (and not of a limiting nature), aluminum chlorohydrate, aluminum chloride, aluminum sesquichlorohydrate, aluminum chlorohydrol-propylene glycol complex, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum dichlorohydrate, aluminum chlorohydrex PG, aluminum chlorohydrex PEG, aluminum dichlorohydrex PG, aluminum dichlorohydrex PEG, aluminum zirconium trichlorohydrex gly propylene glycol complex, aluminum zirconium trichlorohydrex gly dipropylene glycol complex, aluminum zirconium tetrachlorohydrex gly propylene glycol complex, aluminum zirconium tetrachlorohydrex gly dipropylene glycol complex, and mixtures of any of the foregoing. The aluminum-containing materials can be commonly referred to as antiperspirant active aluminum salts. Generally, the foregoing metal antiperspirant active materials are antiperspirant active metal salts.

A particular group of such antiperspirant actives materials includes aluminum chlorohydrate, aluminum dichlorohydrate, aluminum sesquichlorohydrate, aluminum zirconium trichlorohydrate, aluminum zirconium tetrachlorohydrate, aluminum zirconium pentachlorohydrate, aluminum zirconium octachlorohydrate, aluminum zirconium trichlorohydrex gly, aluminum zirconium tetrachlorohydrex gly, and aluminum zirconium pentachlorohydrex gly.

Another particular group of such antiperspirant actives include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG.

A third particular group of such antiperspirant actives include aluminum zirconium trichlorohydrex and aluminum zirconium tetrachlorohydrex either with or without glycine. A particular antiperspirant active is aluminum trichlorohydrex gly such as AZZ-902 SUF (from Reheis Inc., Berkley Heights, N.J.) which has 98% of the particles less than 10 microns in size, but greater than 3 microns in size.

A fourth particular group of such antiperspirant actives include the enhanced efficacy aluminum salts and the enhanced efficacy aluminum/zirconium salt-glycine materials, having enhanced efficacy due to improved molecular distribution, known in the art and discussed, for example, in PCT No. WO92/19221, the contents of which are incorporated by reference in their entirety herein.

More particular examples of such salts include:
Aluminum Chlorohydrate
Chlorhydrol powder, Reach-101, Reach 301, Reach-501, Westchlor 200, Westchlor
DM 200, Summit ACH-325, Summit ACH7-321, and Summit ACH-331.
Aluminum Zirconium Tetrachlorohydrex
Reach AZP-701, Reach AZP-902, Reach AZP-908, Reach AZP-255, Reach AZP-855,
Rezal-36, Westchlor ZR 35B, Summit AZG-368, Summit AZG-369 Summit AZG-370,
Summit Q5-7155 AAZG, and Summit Q5-7167 AAZG.
Aluminum Zirconium Trichlorohydrex
Reach AZZ-902, Reach AZZ-855, Reach AZZ-908, Rezal-33, Westchlor ZR 30B,
Westchlor ZR 58B, Westchlor ZR 60B, Summit Q5-7160 AZAG, and Summit AZG5-7164.
Aluminum Zirconium Octachlorohydrex
Reach AZO-902, Reach AZO-908, and Westchlor ZR82B.
Aluminum Zirconium Pentachlorohydrex
Rezal-67 and Westchlor ZR 80B.
Also, corresponding nitrate, bromide and sulfate salts of any of the foregoing may be used.

In addition, to the Category I active antiperspirant ingredients listed in the Food and Drug Administration's Monograph on antiperspirant drugs for over-the-counter human use, there are other ingredients that can be used, such as tin or titanium salts used alone or in combination with aluminum compounds (for example, aluminum-stannous chlorohydrates), aluminum nitratohydrate and its combination with zirconyl hydroxychlorides and nitrates, can be incorporated as an antiperspirant active ingredient in antiperspirant compositions according to the present invention.

The parent salt is dissolved in an aqueous solvent (preferably water) at a level of between 50%–60% by weight salt concentration based on the weight of the solution. The temperature of the solution can be in the range of 25–90 degrees C., particularly in the range of 50–80 degrees C. (for example, 60±5 degrees C. or 80±5 degrees C.). The aqueous solvent is usually and preferably water, however, the solvent can also contain a minor amount (less than 5%) of alcohols (such as ethanol, propanol or isopropanol), glycols (such as propylene glycol or tripropylene glycol), polyglycols, dimethylisosorbide, sorbitol, glycerine, or mixtures of any combination of the foregoing.

The solution of salt is poured onto a flat surface with a boundary so that it is contained in a fixed area. The thinner the glass formed, the more easily the water can evaporate from the surface and the more homogeneous the composition of the glass. For convenience, the depth of the solution on the surface may be in the range of 0.5–2.0 cm (for example, 1.27 cm (0.5 inch)). At a concentration of 55% and 1.5 cm depth, an area of 60 cm×30 cm may take approximately 2 days to a week to form a glass. Glass formation may optionally be speeded by the application of heat such as in the range of 45–90 degrees C., particularly 60±5 degrees C. and/or the addition of a promoter such as a member selected from the group consisting of borax, sodium phosphates, sodium tetraborate, C2–C3 monocarboxylic acids (and sodium and ammonium salts thereof), C2–C5 dicarboxylic acids (and sodium and ammonium salts thereof), citric acid and aspartic acid, C2–C10 carboxylates, borates including boric acid, and sodium tetraborate, sodium borate, sodium metaborate, boron oxide ($B_2O_3$), oligomers of boric acid, potassium pentaborate, potassium metaborate, sodium triborate, metaboric acid ($HBO_2$), ammonium hydrogen tetraborate, magnesium borate, barium metaborate, calcium metaborate, orthoboric acid, lithium metaborate, lithium tetraborate, zirconium metaborate, and mixtures thereof. Boric acid and sodium tetraborate are promoters of particular interest. The promoter may be used in an amount of 4–10 weight % based on the total weight of the solution of antiperspirant salt. Specific examples of promoters include acetic acid, propionic acid, lactic acid, adipic acid, glutaric acid, maleic acid, diglycolic acid, oxalic acid, succinic acid, malonic acid, citric acid, aspartic acid, sodium acetate, ammonium acetate, ammonium formate, sodium propionate, sodium lactate, sodium succincate, sodium fumarate, sodium maleate, and ammonium citrate. One specific example is ammonium acetate, for example with 6% ammonium acetate. For example, 6% of ammonium acetate in a 50% antiperspirant salt solution may cause the glass to form extremely quickly.

After the glass has been formed it is then broken into pieces small enough to feed into a grinding machine capable of reducing the particles to an average size of 200–1000 microns. On a laboratory scale, this may be done by breaking the glass with a hammer or by hand into centimeter size pieces; however, on an industrial scale, suitable equipment would be used. The pieces are then mixed with a non-aqueous liquid in which the salt is not appreciably soluble (less than 1.0%) such as cyclomethicone (for example, D4, D5, D6 or mixtures thereof), and subjected to an intermediate grinding step (for example, by a homogenization process) to form a suspension having a 15–40% concentration of salt. The intermediate grinding step may be accomplished by feeding the mixture into a suitable grinding machine or a homogenizer (for example, a Ross homogenizer) to further reduce the size of the particles, for example in the range of 200–1000 microns (particularly having an average particle size of 200 microns). Next the broken pieces are subjected to a fine grinding step to reduce the particle size further. This fine grinding step is conducted with equipment capable of reducing the average particle size to about 20 microns or less, particularly less than about 10 microns, more particularly having an average particle size of less than or equal to 2 microns, even more particularly less than or equal to 1.5 microns and, most particularly, less than about 1 micron.

The non-aqueous liquid used as a vehicle is one in which the salt is not appreciably dissolved but, in fact, is suspended. Such a liquid vehicle can be from various categories such as:

(a) cosmetic esters selected from the group consisting of C6–C22 straight or branched chained ethoxylates, propoxylates, benzoates, and adipates;

(b) glycols and polyols selected from the group consisting of propylene glycol and dipropylene glycol;

(c) volatile silicones selected from the group consisting of D4, D5, D6 cyclomethicones and mixtures of any of the foregoing;

(d) non-volatile silicones selected from polydimethicones having a viscosity of up to 350 centistokes;

(e) hydrocarbons such as mineral oils;

(f) alcohols having more than three carbons; and (g) mixtures of any of the foregoing.

Particular examples of such vehicles include the following items in TABLE A.

TABLE A

| Supplier | Tradename | Chemical Name |
| --- | --- | --- |
| Alzo | Dermol 25-3B | C12–C15 ethoxy benzoate |
| Alzo | Dermol 489 | Diethylene Glycol dioctanoate/diisononoate |
| Alzo | Dermol 816 | octyl palmitate |
| Alzo | Dermol DIA | diisopropyl adipate |
| Alzo | Dermol DPG-2B | dipropylene glycol dibenzoate |
| Alzo | Dermol G-76 | Glycereth-7 benzoate |
| Alzo | Dermol PGB | propylene glycol benzoate |
| Alzo | Polyderm PPI-G7 | glycereth-7 polyurethane |
| Amercol | Fluid AP | PPG-14 Butyl Ether |
| BASF | Lutrol OP-2000 | PPG-26 oleate |
| Bernel | Hetester PHA | propylene glycol isoceteth-3 acetate |
| Bernel | Hetester PMA | Propylene Glycol Myristyl Ether Acetate |
| Dow Corning | DC 245 | cyclomethicone |
| Dow Corning | DC 345 | cyclomethicone |
| Finetex | Finsolv EMG-20 | Methyl Gluceth-20 Benzoate |
| Finetex | Finsolv PG-22 | Dipropylene glycol dibenzoate |
| Finetex | Finsolv PL-355 | Poloxamer 105 Benzoate |
| Finetex | Finsolv PL-62 | Poloxamer 182 Dibenzoate |
| Henkel | Cetiol 868 | octyl stearate |
| ISP | Escalol 597 | octocrylene |
| Lipo | Liponate 2-DH | PEG-4 diheptanoate |
| Lipo | Liponate NPGC-2 | neopentylglycol dicaprylate/dicaprate |
| Lipo | Liponate PC | propylene glycol dicaprylate/dicaprate |
| Lipo | Liponate TDS | tridecyl stearate |
| Phoenix | Pelemol G7B | glycereth-7 benzoate |
| PPG | Macol 57 | PPG-10 butane diol |
| PPG | Masil 756 | tetrabutoxy trisiloxane |
| Rhone-Poulenc | benzyl benzoate | benzyl benzoate |
| Rhone-Poulenc | Benzyl Salicylate | benzyl salicylate |
| Scher | DIPSAL | dipropylene glycol salicylate |
| Scher | Schercemol DID | diisopropyl dimer dilinoleate |
| Scher | Schercemol DISD | diisostearyl dimer dilinoleate |
| Trivent | DIDA | diisodecyl adipate |
| Trivent | DOS | Dioctyl sebacate |
| Trivent | OC-G | tricapylin |
| Trivent | PE-48 | pentaerythritol tetraoctanoate |
| Union Camp | Unimate DBS | dibutyl sebacate |
| Union Camp | Unimate DCA | dicapryl adipate |
| Union Camp | Unimate DIPS | diisopropyl sebacate |
| Union Camp | Unimate EHP | 2-ethylhexyl palmitate |
| Vevy | Dodecalene | |
| ALZO | Dermol DPGB | dipropylene glycol benzoate |
| Alzo | Wickenol 159 | dioctyl succinate |
| Amoco | SilkFlo 364 | polydecene |
| BASF | Luvitol EHO | cetearyl octanoate |

TABLE A-continued

| Supplier | Tradename | Chemical Name |
|---|---|---|
| Bernel | Bernel Ester 168 | isocetyl octanoate |
| Bernel | Bernel Ester 2014 | octyldodecyl myristate |
| Bernel | Bernel Ester CO | cetyl octanoate |
| Bernel | Bernel Ester DOM | dicapryl malleate |
| Bernel | Bernel Ester NPDC | neopentyl dicaprate |
| Bernel | Dermol 185 | isostearyl neopentanoate |
| Bernel | Hetester HSS | Isocetyl stearoyl stearate |
| Bernel | Hetester ISS | Isostearyl stearoyl stearate |
| Bernel | Minno 21 | neopentyl glycol dioctanoate/diisostearate |
| Bernel | Minno 41 | neopentyl glycol diisostearate/dioctanoate |
| Finetex | Finsolv P | PPG-15 Stearyl Ether Benzoate |
| ISP | Escalol 507 | octyl dimethyl PABA |
| ISP | Escalol 557 | octylmethoxycinnamate |
| Phoenix | Pelemol 2022 | octyl dodecyl behenate |
| Trivent | OC-16 | cetyl octanoate |
| Trivent | OL-10B | isodecyl oleate |
| Unichema | Prisorine 2036 | 2-ethyl hexyl isostearate |
| Unichema | Prisorine 2039 | isostearyl isostearate |
| Union Camp | Unimate IPP | isopropyl palmitate |
| Union Camp | X81-765-16 | Isopropyl Stearate |
| Vevy | Myristol 2-8-12 | Octyl dodecyl myristate |
| Alzo | Dermol PEB | phenoxyethyl benzoate |
| Alzo | Dermol 89 | octyl isononanoate |
| Alzo | Dermol B246 | benzyl laurate/myristate/palmitate |
| Alzo | Dermol ICSA | Isohexadecyl salicylate |
| Alzo | Dermol IDSA | Isodecyl salicylate |
| Alzo | Dermol TDSA | Isotridecyl salicylate |
| Bernel | Bernel Ester OPG | octyl pelargonate |
| Bernel | Citmol 316 | triisocetyl citrate |
| Bernel | Dermol 105 | isodecyl neopentanoate |
| Bernel | Dermol 126 | laureth-2 benzoate |
| Bernel | Hetester FAO | C12–C15 Alkyl Octanoate |
| Exxon | Isopar M | isoparaffin |
| Exxon | Isopar V | isoparaffin |
| Exxon | Norpar 15 | normal paraffin |
| Fancor | Fancol ID | isododecane |
| Fancor | Fancol IE | isoeicosane |
| Fancor | Fancol IH | isohexadecane |
| Finetex | Finsolv BOD | Octyl Dodecyl Benzoate |
| Finetex | Finsolv EB | 2-ethyl hexyl benzoate |
| Finetex | Finsolv SB | isostearyl benzoate |
| Finetex | Finsolv TN | C12–C15 alkyl benzoate |
| Henkel | Cetiol OE | dicapryl ether |
| Henkel | Cetiol A | hexyl laurate |
| Henkel | Cetiol S | Dioctylcyclohexane |
| ICI | Brij 30 | laureth-4 |
| ISP | Ceraphyl 41 | C12–C145 alkyl lactate |
| ISP | Escalol 587 | octyl salicylate |
| Jarchem | C12/C14 alcohol mix | C12/C14 alcohol mix |
| Jarchem | Jarchol I16 | isocetyl alcohol |
| JarChem | Jarcol I18-T | isostearyl alcohol |
| Jarchem | Jarcol 120 | C20 guerbet alcohol |
| Penta | Hexyl benzoate | hexyl benzoate |
| Phoenix | Pelemol IN-2 | isononyl isononanoate |
| Phoenix | Pelemol ISL | isostearyl lactate |
| PPG | Mazon EE-1 | benzyl laurate |
| Presperse | Permethyl 102A | aliphatic hydrocarbons |
| Trivent | NP-13 | Tridecyl neopentanoate |
| Trivent | OC-13 | tridecyl octanoate |
| Trivent | OS | octyl salycilate |
| Unichema | Prisorine 2021 | isopropyl isostearate |
| Unichema | Prisorine 3515 | isostearyl alcohol |
| Union Camp | Harkamex | C12/C14 alcohol mix |
| Union Camp | Unimate IPIS | isopropyl isostearate |
| Witco | Klearol | light mineral oil |
| Witco | PD-23 | petroleum distillate |
| Witco | PD-28 | petroleum distillate |
|  |  | n-heptane |
|  |  | 1-octanol |
|  |  | lauryl alcohol |
|  |  | isopropyl palmitate |
|  |  | oleyl alcohol |

Particular examples of vehicles include cyclosiloxane (for example, one or more of D4, D5, or D6 cyclomethicones), that may optionally contain a minor amount (less than 5 weight %) of one or more of water, mineral oils, glycols and polyols, and low viscosity fatty esters having 8–18 carbons, provided that the active is still in a suspension and not appreciably dissolved (no more than 5 weight %).

The glycol or polyglycol is selected from the group consisting of ethylene glycol, propylene glycol, 1,2-propanediol, diethylene glycol, triethylene glycol, tetraethylene glycol, dipropylene glycol, tripropylene glycol, methyl propanediol, 1,6-hexanediol, 1,3-butanediol, 1,4-butanediol, PEG-4 through PEG-100, PPG-9 through PPG-34, pentylene glycol, neopentyl glycol, trimethylpropanediol, 1,4-cyclohexanedimethanol, 2,2-dimethyl-1,3-propanediol, 2,2,4,4-tetramethyl-1,3-cyclobutanediol, and mixtures thereof. More particular examples of the glycol component include one or more members of the group consisting of propylene glycol, dipropylene glycol, tripropylene glycol, 2-methyl-1,3-propanediol, methyl propylene glycol, low molecular weight (less than 600) polyethylene glycol, low molecular weight (less than 600) polypropylene glycols, and mixtures of any of the foregoing. Tripropylene glycol has lower irritancy. Mixtures of glycols may be used to balance these desirable properties. (This definition of glycol is the same for any use of that term in this application.)

It should also be noted that the viscosity of such vehicle must be considered in relationship to the grinding equipment, with heavier equipment being able to handle higher viscosity materials. Viscosity modifying agents (for example, surfactants) can be added as needed as long as the active salt is not soluble in the viscosity modifying agent and as long as the equipment is capable of processing the total mixture.

In general the processing itself is used to reduce the average particle size so that it does not exceed about 20 microns, especially not exceeding about 10 microns and, more particularly, having at least 50% of the particles with a size below 1.10 microns. As described below, enhanced salts can be prepared having an average particle size less than or equal to 0.5 microns with some particles approaching 0.2–0.3 microns.

The process of this invention not only reduces the size of the particles, it also changes the distribution of the molecular species of aluminum and zirconium within the particles. This may be ascertained, for example, by the analytical techniques described in U.S. Ser. No. 9/597,322 (incorporated by reference in its entirety as to the description of the analytical techniques described therein), or by other techniques available in the art.

In order to implement the process, appropriate equipment must be used. In selecting appropriate equipment, various choices are available and several processing factors should be considered:

Media Balls

Examples of suitable balls include 0.2 mm–0.4 mm yttrium-stabilized Zirconium Oxide (TZP) for both media hardness and grinding performance. These are commercially available (for example, from Tosoh Ceramics, Japan). Smaller balls may be made or purchased from other sources now or in the near future such as those having a 0.075 size. Other materials include soda lime glass, zirconium toughened alumina and steel.

Mill

Examples of suitable mills include a number of those described in Perry's Chemical Engineering Handbook (7th Edition) as limited by the particle sizes required for the invention (see Tables 20–6 and 20–7 at pages 20–23). Suitable types of size reduction equipment include:

(1) Media Mills such as (a) Ball, pebble, rod and compartment mills (batch and continuous); (b) Autogenous tumbling mills; (c) Stirred ball and bead mills (for example, LME 1 unit from Netzsch Inc. (Exton, Pa.) which incorporates an ultra high molecular weight (UHMW) liner, rotor and rotor shaft to minimize product contamination during the grinding operation as opposed to an all stainless steel mill; and (d) Vibratory mills. Such equipment may be obtained from one or more of the following companies: Draiswerke (Mahwah, N.J.); and Netzsch, Inc. (Exton, Pa.).

(2) Medium peripheral-speed mills such as (a) Ring-roll and bowl mills; (b) Roll mills, cereal type; (c) Roll mills, paint and rubber type; (d) Buhrstones.

(3) High-peripheral-speed mills such as (a) Fine grinding hammer mills; (b) Pin mills; (c) Colloid mills; (d) Wood pulp beaters.

Fluid energy superfine mills such as (a) Centrifugal jet; (b) Opposed jet; (c) Jet with anvil; and (d) Fluidized-bed jet.

Media mill grinding is of particular interest. Media mill grinding uses selected media to accomplish size reduction either as a wet or dry process with the exception of the autogenous tumbling mills which use larger lumps of the material to be ground as the grinding media. With tumbling or vibratory mills, the external vessel provides the motion necessary for the media to accomplish the required grinding. The stirred ball and bead mills use a fixed vessel (sometimes with recirculation loops) and a high speed rotor to achieve the grinding performance required. The LME 1 unit described above is capable of generating 1.0 micron particles when used with the method of this invention.

Vibratory mills are also capable of 1.0 micron particle sizes in dry form.

Temperature Control

Much of the energy used in grinding applications evolves into heat. By some estimates up to 98% of grinding energy can be lost as heat. It is preferred that chilled water (for example, in the 0–5 degree C. range) around a jacketed vessel be used to maintain temperature control.

Viscosity Build-Up

Experimental work done for this invention used active-in-silicone systems from 15–40% concentration as the starting material. In all cases significant viscosity increases were observed due to the enormous increase in the surface area of the active particles and subsequent particle-particle interactions. Viscosity reduction agents such as lecithin and other surfactants can be used to control the buildup for ease in processing. It is to be noted, however, that this increase in viscosity can also be used to reduce the amount of thickeners or gelling agents needed for the final cosmetic products.

The process is carried out by mixing the active salt with a vehicle selected to be one or more members from the group described above. The salt is not appreciably soluble in the vehicle (less than 5%) and is suspended in the vehicle in a concentration of 15–40% by weight, especially 20–30% and, particularly 25%. The suspension is then ground at a temperature in the range of 20–70 degrees C. to an average particle size of less than or equal to 2 microns, particularly less than or equal to 1.5 microns, especially and preferably where at least 50% by weight of the salt has a particle size below 1.10 microns. The process is carried out without the use of added water or external heating and, in fact, may require cooling to maintain temperature to form the enhanced salts of the invention The enhancement of the salt can be monitored by certain analytical techniques. Examples of several techniques have been described above. These include SEC, GPC and various modifications of such techniques. In one method the SEC or GPC columns separate the aluminum and zirconium species by molecular size, using a photodiode array detector connected to the column outlet. The eluent fractions from the SEC or GPC may be evaluated further by analysis of the individual fractions by ICP. In a second method, (which is used in some of the examples below), SEC may be directly coupled to ICP. The eluent fractions passing through the column are directly linked to the ICP unit; the ICP unit in this case is used as a detector. Data points are collected such as, for example, one data point every 6 seconds. It should be noted that the identity of the peaks using the SEC test described in Example 1S below was previously verified in other work wherein the ICP system was used as a detector. This previous work was done in order to obtain a profile for the antiperspirant active salt. An ICP unit is directly coupled to an HPLC unit in which the column has been selected to be an organically coated silica as an SEC system. The ICP unit is used as a detector so that the oligomeric fractions separated by the SEC column are elucidated on-line quantitatively for Al, Zr and other elements. The ICP's detector is, for example, a simultaneous charge induction device (CID) with a wavelength of 175 to 800 nm. The eluent from the SEC column is analyzed and a data point is noted periodically such as about once every six seconds for Al and Zr. The data points collected are plotted against retention time, to form the chromatogram for each element separately. The number for the individual peak areas represents the relative concentration for that specific element. (See discussion in U.S. Pat. No. 5,997,850.) The method described in Example 1S is a more commercially viable method for a manufacturing environment.

It should be noted that normal detection methods do not measure a related increase in another peak as being associated with a smaller zirconium species. It has been shown that the smaller zirconium species are absorbed on the column. See U.S. Pat. No. 5,997,850. This is verified by reforming the larger zirconium species with dilution. The dilution of the enhanced salt in water causes the larger zirconium species to reform and, thus, Peak 1 will increase to reflect the re-formation of the larger species. It is noted that Peak 1 is exclusively larger zirconium species and he remaining peaks are all aluminum species.

Formulated Products

In its third aspect this invention also includes cosmetic products such as antiperspirants and/or deodorants which are made with the enhanced active salts from the inventive process described above. The formulations of this invention may be made by conventional techniques such as those described in Cosmetics and Toiletries Industry (second edition, 1996) (Chapman and Hall, NY, N.Y.). The enhanced salt is used in place of the normally used active salt, however, mixtures of enhanced salt and traditional salt may be used (for example, because of cost considerations). The use of an enhanced salt of the invention results in improved efficacy, a reduction in the amount of thickener that is needed and improved aesthetics. The activated salts of this invention can be used in a wide variety of formulations, and in any products which call for the inclusion of antiperspirant salts, provided the formulations are:

(a) anhydrous (no more than 5% water);
(b) do not contain methanol, ethanol or isopropanol in an amount greater than 5%; and
(c) the total amount of glycol component (propylene glycol, dipropylene glycol, tripropylene glycol, polypropylene glycol, etc.) does not exceed 50% by weight of the amount of enhanced antiperspirant active salt in the finally formulated cosmetic product (for example, an antiperspirant or deodorant).

The formulated products of this invention include antiperspirants (where a sufficient amount of salt is added to have an antiperspirant effect) and deodorants (where a lower level of an antiperspirant salt can be used). In traditional compositions antiperspirant actives can be incorporated into compositions in amounts in the range of 0.1–25% of the final composition; the amount used will depend on the formulation of the composition. For example, at amounts in the lower end of the broader range (for example, 0.1–10% on an actives basis), a deodorant effect may be observed. At lower levels the antiperspirant active material will not substantially reduce the flow of perspiration, but will reduce malodor, for example, by acting as an antimicrobial material. At amounts of 10–25% (on an actives basis) such as 15–25%, by weight, of the total weight of the composition, an antiperspirant effect may be observed. The antiperspirant active material is desirably included as particulate matter suspended in the composition of the present invention in amounts as described above, but can also be added as solutions or added directly to the mixture. It is also believed that lower amounts of the activated salts can be used to achieve the desired effects that have usually required higher amounts of regular salts or activated salts having larger particle sizes.

With respect to various types of formulations in which the activated salts of this invention may be useful, the following types are included. These formulations may be viewed as suspensions which have the appearance of a clear gel but without some of the less desirable characteristics of gels such as wetness. Other formulations may be made which are translucent or opaque. The physical forms of these formulations include sticks, gels, creams, soft solids, roll-ons, pump sprays and aerosols.

This invention includes improved salts, a process for making the improved salts and formulations of antiperspirants and/or deodorants made with the improved salts. While stick, gel, cream, soft solid, roll-on, spray and aerosol products may be formed with the salts of the invention, it is currently believed that roll-on or spray products will give the highest efficacy. Particular examples include (a) silicone based soft solid formulae where the systems are thickened with selected polysiloxane polyamides;
(b) silicone based stick formulae where the systems are thickened with selected polysiloxane polyamides;
(c) pump sprays where the active is suspended in a suitable vehicle; and
(d) aerosols where the active is suspended in a suitable vehicle (such as cyclomethicone) and a hydrocarbon or hydrofluorocarbon propellant (such as blended butanes) is used.

Formulated products made with the enhanced salts of the invention include those made with gelling agents to increase viscosity when desired and/or to form more structured products. In terms of suitable gelling agents, C10–40 straight chain alcohols (especially stearyl alcohol), paraffins (for example, those having a melting point in the range of 54–90 degrees C.), 12-hydroxy stearic acid, Japan wax, dibutyl lauryl glutamide, selected polyamides, certain types of polyethylenes and dibenzylidene sorbitol may be used. Suitable polyethylenes include those having a molecular weight in the range of 200–5,000, with a melting temperature in the range of 50–150 degrees C. and a polydispersity in the range of 1–10 (such products are available from New Phase Technology, Piscataway, N.J.). If clear products are desired, selected polyamides as described herein may be used.

In general, the polyamides useful in this invention as gelling agents are those described in U.S. Pat. No. 6,051,216. These polyamides are multiples of a unit represented by the following Formula A:

Formula A

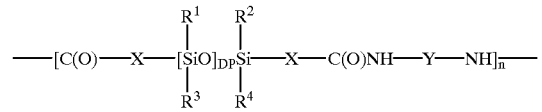

where:
(1) DP is selected from the group consisting of 1–700, preferably 15–500, and more preferably 15–45. DP represents an average value for degree of polymerization of the siloxane units in the polymer with greater or lesser DP values centered around the indicated DP value.
(2) n is a number selected from the group consisting of 1–500, particularly 1–100, more particularly 4–25.
(3) X is a linear or branched chain alkylene having 1–30 carbons, particularly 3–10 carbons and, more particularly, 10 carbons.
(4) Y is selected from the group consisting of linear or branched chain alkylenes having 1–40 carbons, particularly 1–20 carbons, more particularly 2–6 carbons and, especially 6 carbons, wherein
  (a) The alkylene group may optionally and additionally contain in the alkylene portion at least one of (i) 1–3 amide linkages; (ii) C5 or C6 cycloalkane; and (iii) phenylene optionally substituted by 1–3 members selected independently from the group consisting of C1–C3 alkyls; and
  (b) the alkylene group itself may optionally be substituted by at least one member selected from the group consisting of (i) hydroxy; (ii) C3–C8 cycloalkane; (iii) 1–3 members selected independently from the group consisting of C1–C3 alkyls; phenyl optionally substituted by 1–3 members selected independently from the group consisting of C1–C3 alkyls; (iv) C1–C3 alkyl hydroxy; and (v) C1–C6 alkyl amine; or Y=Z where Z=T($R^{20}$)($R^{21}$)($R^{22}$) where each of $R^{20}$, $R^{21}$ and R22 are independently selected from the group consisting of linear and branched C1–C10 alkylenes; and T is selected from the group consisting of CR, where R is selected from hydrogen, the group consisting of the group defined for $R^1$–$R^4$, and a trivalent atom selected from N, P and Al.
(5) Each of $R^1$–$R^4$ (collectively "R") is independently selected from the group consisting of methyl, ethyl, propyl, isopropyl, a siloxane chain, and phenyl, wherein the phenyl may optionally be substituted by 1–3 members from the group consisting of methyl and ethyl. More particularly, values for $R^1$–$R^4$ are selected from methyl and ethyl and especially methyl.

The values for X, Y, DP, and $R^1$–$R^4$ may be the same or different for each unit of the polyamide.

Preferred polysiloxane polyamides suitable for use in the antiperspirants and/or deodorants of this invention include those described in WO 99/06473. For the sake of clarity similar nomenclature is used here with the modifications as needed for the invention. This general description is followed by the particular description of the siliconized polyamides which give the superior results reported here. For the general description, these polyamides are multiples of a unit represented by the following Formula IIIA:

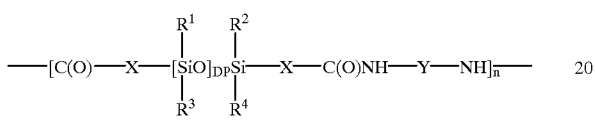

Formula IIIA where:
(1) DP is a number in the range of 5–30, particularly 5–20, more particularly 12–18, and especially 15. DP represents an average value for degree of polymerization of the siloxane units in the polymer with greater or lesser DP values centered around the indicated DP value;
(2) n is a number selected from the group consisting of 1–500, particularly 20–200, and, more particularly, 40–100, where n is also an average value;
(3) X is a linear or branched chain alkylene having 1–30 carbons, particularly 3–10 carbons and, more particularly, 10 carbons;
(4) Y is selected from the group consisting of linear and branched chain alkylenes having 1–40 carbons, particularly 1–20 carbons, more particularly 2–6 carbons and, especially 6 carbons, wherein
   (a) the alkylene group may optionally and additionally contain in the alkylene portion at least one of the members of a group consisting of (i) 1–3 amide linkages; (ii) C5 or C6 cycloalkane (as a cycloalkylene linkage); and (iii) phenylene optionally substituted by 1–3 members selected independently from the group consisting of C1–C3 alkyls; and
   (b) the alkylene group itself may optionally be substituted by at least one member selected from the group consisting of (i) hydroxy; (ii) C3–C8 cycloalkane; (iii) 1–3 members selected independently from the group consisting of C1–C3 alkyls; phenyl optionally substituted by 1–3 members selected independently from the group consisting of C1–C3 alkyls; (iv) C1–C3 alkyl hydroxy; and (v) C1–C6 alkyl amine; or Y=$Z^2$ where

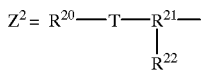

wherein each of $R^{20}$, $R^{21}$ are independently selected from the group consisting of linear and branched C1–C10 alkylenes; $R^{22}$ is selected from the group consisting of linear and branched C1–C10 alkanes; and T is selected from the group consisting of (1) a trivalent atom selected from N, P and Al; and (2) —CR, where R is selected from the group consisting of hydrogen, methyl, ethyl, propyl, isopropyl, a siloxane chain, and phenyl, wherein the phenyl may optionally be substituted by 1–3 members from the group consisting of methyl and ethyl, especially methyl and ethyl and most especially methyl; and
(5) each of $R^1$–$R^4$ is independently selected from the group consisting of methyl, ethyl, propyl, isopropyl, a siloxane chain, and phenyl, wherein the phenyl may optionally be substituted by 1–3 members from the group consisting of methyl and ethyl (with more particular values for $R^1$–$R^4$ being selected from methyl and ethyl and especially methyl;

provided that in making clear cosmetic stick formulations, at least 8% of the final composition is a polyamide of Formula IIIA where the DP is in the range of 12–18 and especially 15.

The values for X, Y, DP, and $R^1$–$R^4$ may be the same or different for each unit of the polyamide.

By siloxane groups is meant groups having siloxane units:

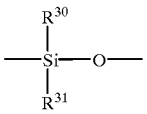

where $R^{30}$ and $R^{31}$ are each independently selected from the group consisting of organic moieties, and each of $R^{30}$ and $R^{31}$ are connected to the silicon by a carbon-silicon bond.

The carbon numbers in the alkylene chain do not include the carbons in the extra segments or substitutions. Also, the polyamides must have a siloxane portion in the backbone and optionally may have a siloxane portion in a pendant or branched portion.

If repeated with no variations in the defined variables, Formula IIIA is representative of a linear homopolymer. Acceptable variations of the invention include: (1) polyamides in which multiple values of DP, X, Y, and $R^1$–$R^4$ occur in one polymeric molecule, wherein the sequencing of these units may be alternating, random or block; (2) polyamides in which an organic triamine or higher amine such as tris(2-aminoethyl)amine replaces the organic diamine in part, to produce a branched or crosslinked molecule; and (3) physical blends of any of (1) and (2) and/or linear homopolymers.

Particular examples of compounds of Formula IIIA include the following:
1) Polyamides of Formula IIIA where the values for X, Y, n, and DP are the same as defined in Formula IIIA, and $R^1$–$R^4$ are each methyl;
2) Polyamides of Formula IIIA where the DP is in the range of 5–30;
3) Polyamides of Formula IIIB:

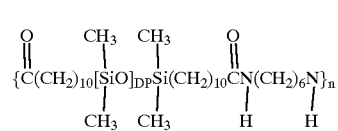

Formula IIIB where DP is from 5–30 and n has the same value as in Formula IIIA;
4) Polyamides of Formula IIIB wherein the DP is from 5–20;
5) Polyamides of Formula IIIB wherein the DP is from 12–18;
6) Polyamides of Formula IIIB wherein the DP is 15;
7) Polyamides of Formula IIIA where the values of X, Y, DP and $R^1$–$R^4$ remain the same in each unit of the polymer;
8) Polyamides of Formula IIIB where the value of DP and n remain the same for each unit of the polymer;
9) Polyamides of Formula IIIA containing multiple siloxane block lengths as shown in Formula IIIC:

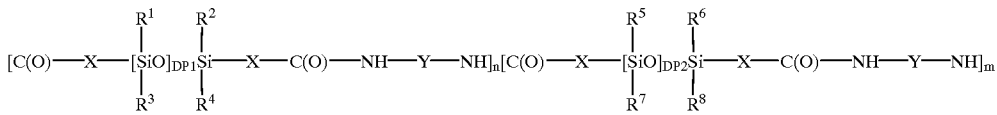

Formula IIIC where X, Y, n, and $R^1$–$R^4$ have the meanings described above for Formula IIIA; m is selected from the same groups as defined for n, and n and m denote the total number of units enclosed within the brackets, with the individual units arranged with regular, alternating, block or random sequencing; $R^5$–$R^8$ is selected from the same group as defined for $R^1$–$R^4$; DP1 and DP2 may be the same or different and are each independently selected from the same group as defined for DP; and the units denominated by n and m may be structured to form either block (regularly sequenced) or random copolymers.

10) Polyamides of Formula A containing siloxane block lengths of Formula IIIC wherein all of the R groups are selected to be methyl.
11) Polyamides of Formula IIIA containing siloxane block lengths of Formula IIIC wherein DP1=DP2.
12) Polyamides of Formula IIIA containing siloxane block lengths of Formula IIIC wherein all of the R groups are selected to be methyl and DP1=DP2.
13) Polyamides synthesized from multiple diamines as shown in Formula IIID:

where X, Y, $Y^1$, $R^1$–$R^8$, m, n, DP1–DP2, have the same values as defined above; $R^9$–$R^{12}$ are selected from the same group as defined for $R^1$–$R^8$, DP3 is selected from the same group as defined for DP; and p is selected from the same groups as defined for m and n;

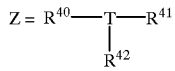

wherein $R^{40}$, $R^{41}$ and $R^{42}$ are each independently selected from the group consisting of linear and branched C1–C10 alkylenes, and T is selected from the group consisting of (1) and a trivalent atom selected from N, P and Al; and (2) CR, where R is selected from hydrogen and the same group as defined for $R^1$–$R^4$. Preferred values for p are 1–25 with more preferred values being 1–7. Preferred values for $R^1$–$R^{12}$ are methyl. A preferred value for T is N. Particular values for each of DP1–DP3 are 5–30, particularly 5–20, more particularly 12–18 and especially 15. A preferred value for each of $R^{40}$, $R^{41}$ and $R^{42}$ is ethylene. A preferred value for Z=(—$CH_2CH_2$)$_3$N.

A particular group of compounds of Formula IV are those of Formula IVA:

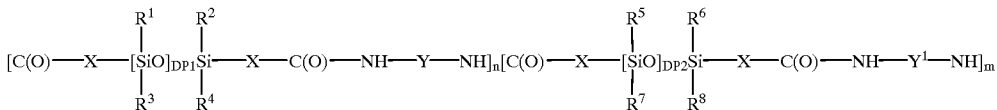

Formula IIID where X, Y, m, n, and $R^1$–$R^8$, DP1, DP2 have the same meanings as described above for Formula IIIA and Formula IIIC; $Y^1$ is independently selected from the same group as defined for Y; and the units denominated by n and m may be structured to form either block (regularly sequenced) or random copolymers.

14) Polyamides of Formula IIID where DP1=DP2.
15) Polyamides of Formula IIID where all of the R groups are selected to be methyl.
16) Polyamides of Formula IIID where all of the R groups are selected to be methyl and DP1=DP2.

Another related class of polyamides may be synthesized with trifunctional amines as shown in Formula IV:

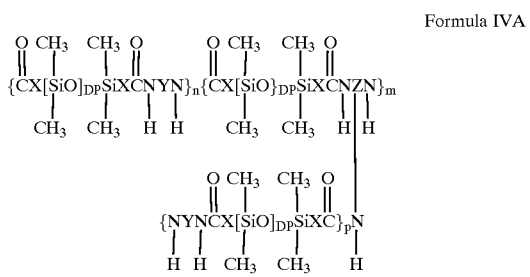

Formula IVA

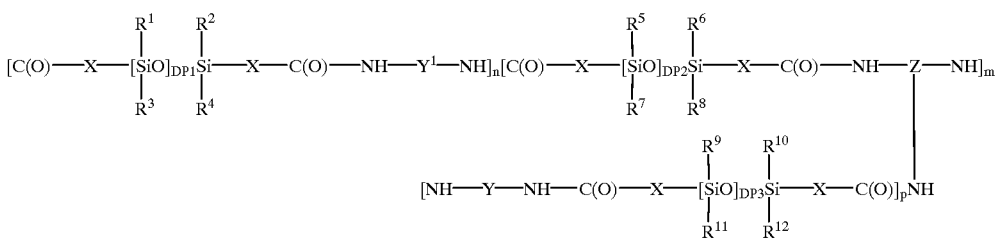

Formula IV where $X=-(CH_2)_{10}-$, $Y=-(CH_2)_6-$; DP=15–45; m=5–20% of m+n+p; and $Z=(-CH_2CH_2)_3N$; m=2–500; n=2–500; p=2–500; provided m=5–20% of m+n+p and m, n, and p are selected so that the average molecular weight is at least 50,000 daltons.

In general, the siloxane-based polyamides (1) contain both siloxane groups and amide groups to thicken compositions containing silicone fluids (volatile and/or non-volatile silicone fluids); (2) are non-flowable solids at room temperature; and (3) dissolve in a fluid which contains silicone at a temperature of 25–160 degrees C. to form a translucent or clear solution at a temperature in this range.

With regard to the siloxane units in the siloxane-based polyamides, the siloxane units must be in the main or backbone chain but can also optionally be present in branched or pendent chains. In the main chain the siloxane units occur in segments as described above. In the branched or pendent chains the siloxane units can occur individually or in segments.

Particular groups of siloxane-based polyamides include:

(a) polyamides of Formula IIIA whore DP is a number in the range of 5–30, particularly 15–20, more particularly 12–18 and especially 15, provided that at least 8% of the composition is a polyamide of Formula IIIA with a DP in the range of 12–18, especially 15;

(b) physical blends of two or more polyamides described above in Formulae IIIA, IIIB, IIIC, IIID, IV and IVA, wherein (1) at least 80% of the blend is at least one polyamide as described above for this invention with a DP in the range of 5–30 with at least 8% of the final cosmetic composition being a polyamide of Formula IIIA with a DP in the range of 12–18, especially 15; and (2) the remainder of the blend is a polyamide of the Formulae IIIA, IIIB, IIIC, IIID, IV, or IVA, except that the DP value is a number in the range of 45–500, or blends of these higher DP materials;

(c) compounds of Formula IIIC where (1) the value for DP1=5–30 and the value for DP2=5–500 and (2) the portion of the polyamide having DP1 is about 1–99 weight % based on the weight of the total polyamide content and the portion of the polyamide having DP2 is about 1–99 weight % with at least 8% of the final cosmetic composition being a polyamide of Formula IIIC with a DP in the range of 12–18, especially 15;

(d) physical blends of polyamides of Formula IIIB made by combining (1) 60–99 weight % of a polyamide where DP=5–30 and especially where DP=10–20, and (2) 1–20 weight % of a polyamide where DP=5–500, especially where DP=45–100 with at least 8% of the final cosmetic composition being a polyamide of Formula IIIB with a DP in the range of 12–18, especially 15;

(e) polyamides of Formula IIID where at least one of Y and $Y^1$ contains at least one hydroxyl substitution with at least 8% of the final cosmetic composition being a polyamide of Formula IIID with a DP in the range of 12–18, especially 15;

(f) polyamides of Formula IIIA synthesized with at least a portion of an activated diacid (diacid chloride, dianhydride or diester) instead of the diacid, with at least 8% of the final cosmetic composition being a polyamide of Formula IIIA with a DP in the range of 12–18, especially 15;

(g) polyamides of Formula IIIA where $X=-(CH_2)_3-$ with at least 8% of the final cosmetic composition being a polyamide of Formula IIIA with a DP in the range of 12–18, especially 15;

(h) polyamides of Formula IIIA where $X=-(CH_2)_{10}-$ with at least 8% of the final cosmetic composition being a polyamide of Formula IIIA with a DP in the range of 12–18, especially 15;

(i) polyamides of Formula IIIA where the polyamides are made with a monofunctional chain stopper selected from the group consisting of monofunctional amines, monofunctional acids, monofunctional alcohols, including fatty acids, fatty alcohols and fatty amines, such as, for example: octylamine, octanol, stearic acid and stearyl alcohol with at least 8% of the final cosmetic composition being a polyamide of Formula IIIA with a DP in the range of 12–18, especially 15.

Polyamides of this invention can be used as a thickening agent in compositions containing silicone fluids to form creams (for example, semi-solid or soft solid), gels and sticks; thus, both soft (and mushy) or firm (and hard) compositions can be formed. The firmness of the product will depend on the amount of the gelling agent(s) used.

In general, when using polyamides of Formula IIIA to make antiperspirants and/or deodorants, an amount of polyamide equal to at least 8% by weight based on the final weight of the total antiperspirant and/or deodorant product should be used for a clear stick (or a minimum of 4% for a clear soft solid). This is especially true if a polyamide of Formula IIIA having a DP=15 is used. If a polyamide with a DP=30 is used, about 5–15% more polyamide must be used to obtained the same rheological consistency.

In one particular series of formulations of antiperspirant and/or deodorant products, the following Table B can be used to determine how much of what type of polyamide gellant of Formula IIIA to use in the final formulations. Additionally, a blend of polyamides of Formula IIIA having different DP's (in the range of 5–30) can be used, provided that there is a minimum of 8% (4% for soft solids) of the polyamide having a DP in the range of 12–18 (especially 15).

TABLE B

| Percent of Polyamide Gellant in Final Product | Degree of Polymerization | Failure Stress Test Results from 3-Point Bending Test (Pascal units) |
| --- | --- | --- |
| 15% | 15 | 11.9 |
| 23% | 15 | 25.6 |
| 30% | 15 | 40.1 |
| 15% | 30 | 9.7 |
| 23% | 30 | 17.5 |
| 30% | 30 | 28.1 |

Another type of gelling agent that may be used either alone or in combination with other gelling agent listed herein is elastomers such as:

(a) a dimethicone/vinyldimethicone crosspolymer composition made by reacting (in the presence of a platinum catalyst) a polymethylhydrogensiloxane with an alpha, omega-divinylpolydimethyl siloxane for which the dimethicone/vinyldimethicone crosspolymer composition (1) is used at a concentration of 4–10% in cyclomethicone (particularly 4–7%, and, more particularly, 4–6.5%) (for example, where the cyclomethicone is a D4 or D5 cyclomethicone), (2) has a refractive index in the range of 1.392–1.402 at 25 degrees C., and (3) has a viscosity in the range of 0.013–1×10$^4$ Pascal seconds (for example, KSG-15 silicone elastomer from Shin-Etsu Silicones of America (Akron, Ohio); and (b) a cyclomethicone (and) dimethicone crosspolymer made with an $\equiv$Si—H containing polysiloxane and an alpha, omega-diene of formula $CH_2=CH(CH_2)_x$ $CH=CH_2$, where $x=1-20$, to form a gel by crosslinking and addition of $\equiv Si-H$ across double bonds in the alpha, omega diene, which crosspolymer has a viscosity in the range of 50,000–3,000,000 centipoise (particularly 100,000–1,000,000; more particularly 250,000–450,000 centipoise; and most particularly 350,000 centipoise), preferably with a nonvolatiles content of 8–8% (particularly 10–14% and most particularly 12–13%) in cyclomethicone (for example a D4 or D5 cyclomethicone), (an example of such a crosspolymer composition being DC-9040 from Dow Corning Corporation (Midland, Mich.) with other types of such crosspolymers (also called elastomers) being described in U.S. Pat. No. 5,654,362, incorporated by reference herein as to the description of such polymers and methods of making such polymers);

Particular examples of suitable elastomers are SFE 167, a cetearyl dimethicone/vinyl dimethicone crosspolymer from GE Silicones (Waterford, N.Y.); SFE168, a cyclomethicone (and) dimethicone/vinyl dimethicone crosspolymer from GE Silicones; vinyl dimethicone crosspolymers such as those available from Shin Etsu Silicones of America (Alron, Ohio) under trade names KSG-15 (cyclomethicone (and) dimethicone/vinyl dimethicone crosspolymer), KSG-16 (dimethicone (and) dimethicone/vinyl dimethicone crosspolymer), KSG-17 (cyclomethicone (and) dimethicone/vinyl dimethicone crosspolymer), KSG-18 (phenyl trimethicone (and) dimethicone/phenyl vinyl dimethicone crosspolymer); and KSG-20 (dimethicone copolyol crosspolymer; dimethicone/vinyl dimethicone crosspolymer from Dow Corning Corporation (Midland, Mich.) under trade name Dow Corning 9506 Cosmetic Powder, DC-9040 elastomer in cyclomethicone from Dow Corning; and a mixture of cyclomethicone and stearyl-vinyl/hydromethylsiloxane copolymer available from Grant Industries, Inc. (Elmwood Park, N.J.) under the trade name Gransil SR-CYC.

More specific formulations for products made with the salts of this invention include:

Clear Stick
- 0.5–50% antiperspirant active of the invention
- 20–80% cyclomethicone (particularly D5 and/or D6 cyclomethicone)
- 0–50% emollients (particularly fatty esters having 6–18 carbons such as PPG-3-myristyl ether)
- 10–15% of a polyamide of Formula IIIA with a DP=15

Translucent/Opaque Stick
- 0.5–50% antiperspirant active of the invention
- 20–80% cyclomethicone (particularly D5 and/or D6 cyclomethicone)
- 0–50% emollients (particularly fatty esters having 6–18 carbons such as PPG-3-myristyl ether)
- 10–15% of a gellant selected from the group consisting of stearyl alcohol, 12-hydroxy stearic acid, dibutyl lauryl glutanamide, and polyethylenes of the type described above under suitable gelling agents, and paraffins having a melting point in the range of 54–90 degrees C.

Clear Soft Solid
- 0.5–50% enhanced active salt of the invention
- 20–80% cyclomethicone
- 4–10% polyamide of Formula IIIA or 0.2–2% (particularly 0.5%) of an elastomer selected from the group described above as a gellant
- 0–50% emollients (for example fatty esters having 6–18 carbons such as C12–15 alkyl benzoates)
- 0–3% fragrance.

Translucent/Opaque Soft Solid

These products may be made as described for the Clear Soft Solid products but without the use of polyamides or elastomer gelling agents.

Roll-on
- 20–90% cyclomethicone
- 0–20% dimethicone (up to 350 centistokes)
- 0.5–50% enhanced active of the invention
- 0–3% fragrance.

Aerosol
- 5–30% cyclomethicone
- 0–20% dimethicone (up to 350 centistokes)
- 0–10% quaternium-18 hectorite
- 0.5–50% enhanced active made of the invention
- 50–80% propellant (for example, blended butanes)
- 0–3% fragrance Pump Spray Same as aerosol formulation without the propellant.

The release of antiperspirant actives into the sweat is a significant event in the development of an antiperspirant effect. The magnitude of the antiperspirant effect is related to the concentration of the antiperspirant salt in the sweat concentration. It is well known that the smaller species are more desirable that the larger species in terms of antiperspirant activity. (See *Antiperspirants and Deodorants*, edited by Karl Laden, second edition, (Marcel Dekker, Inc., N.Y., N.Y. 1999), especially Chapter 4.)

The ability of the enhanced salt to act as an antiperspirant active can be verified by diluting a solution of an enhanced active as made by the method of the invention in water and observing the reformation of the Peaks assigned to the larger Al and Zr species (Peak 1 for zirconium and Peak 3 for aluminum). It should be noted that in formulating the antiperspirant and/or deodorant compositions of this invention, some forms may be more amenable to releasing the actives. For example, roll-ons and sprays appear to release the actives in an improved way compared to stick products.

The cosmetic composition according to the present invention can be packaged in conventional containers, using conventional techniques. For example, where the composition is a stick composition, the composition, while still in liquid form, can be introduced into a dispensing package as conventionally done in the art, and cooled therein so as to thicken in the package. Where a gel or soft-solid cosmetic composition is produced, the composition can be introduced into a dispensing package (for example, a package having a top surface with pores) as conventionally done in the art. Thereafter, the product can be dispensed from the dispensing package as conventionally done in the art, to deposit the active material, for example, on the skin. This provides good deposition of the active material on the skin.

Throughout the present specification, where compositions are described as including or comprising specific components or materials, or where methods are described as including or comprising specific steps, it is contemplated by the inventors that the compositions of the present invention also consist essentially of, or consist of, the recited components or materials, and also consist essentially of, or consist of, the recited steps. Accordingly, throughout the present disclosure any described composition of the present invention can consist essentially of, or consist of, the recited components or materials, and any described method of the present invention can consist essentially of, or consist of, the recited steps.

As mentioned previously, the present invention includes within its scope (but is not limited to) creams, "soft gels" and sticks. The stick form can be distinguished from a soft gel in that, in a stick, the formulated product can maintain its shape for extended time periods outside the package, the product not losing its shape significantly (allowing for some shrinkage due to solvent evaporation). Soft gels can be suitably packaged in containers which have the appearance of a stick, but which dispense through apertures (for example, slots or pores) on the top surface of the package.

In the cosmetic field, systems are classified as soft gels or sticks, depending on their viscosity or hardness alone; typically, it is understood that soft gels are soft, deformable products while sticks are strictly free-standing solids. For example, by rheological analysis, a commercial deodorant stick has been determined to have a plateau storage modulus $G'(\omega)$ of roughly $10^5$ Pa and a complex viscosity of $10^6$ Pa second, both at an angular frequency of 0.1 rad/sec). On the other hand, a commercial antiperspirant soft gel has been determined to have a $G'(\omega)$ value of roughly $10^3$ Pa and a complex viscosity of $10^4$ Pa second (at 0.1 rad/sec). Use of the present glycol component provides particularly good results in connection with soap-based compositions (for example, deodorant gel compositions gelled utilizing a soap gelling agent).

The following Examples are offered as illustrative of the invention and are not to be construed as limitations thereon. In the Examples and elsewhere in the description of the invention, chemical symbols and terminology have their usual and customary meanings. Temperatures are in degrees Celsius unless otherwise indicated. The amounts of the components in the Examples as well as elsewhere in the application, are in weight percents based on the standard described; if no other standard is described then the total weight of the compositions is to be inferred. Various names of chemical components used in this application include those listed in the *CTFA International Cosmetic Ingredient Dictionary* (Cosmetics, Toiletry and Fragrance Association, Inc., $4^{th}$ ed. 1991).

EXAMPLES

Process Examples

Example 1P—General Process

Glass Formation Method #1

A sample of an antiperspirant powder as received from the vendor is dissolved in water at a concentration in the range of 50–60% by weight based on the weight of the mixture. Heating (for example, in the range of 30–99.9 degrees C., more particularly 50–80 degrees C.) may be used to speed up the dissolution process. For this method #1, a temperature of about 80 degrees C. is used. The solution is then poured into a flat pan to a depth of 0.05–20 cm (particularly 1–2 cm) and exposed to the air to allow the water to evaporate. For this method #1 a depth of about 1 cm is used. A glass state will be formed after about 1–2 weeks at room temperature depending on the concentration of the solution. For this method #1 the glass forms in about 2–3 days.

Glass Formation Method #2

Glass Formation Method #1 is repeated except that a promoter is used such a member selected from the group consisting of those described above with a particular group being ammonium acetate, sodium tetraborate, sodium propionate and sodium lactate. The promoter is added to the solution of water and antiperspirant active. One particular method uses 6% ammonium acetate in a 50% antiperspirant/water solution, and results in almost instantaneous formation of a glass.

Breaking Step

After the glass is formed, it is broken into pieces of about 1 $cm^2$ by hand or using a hammer or other suitable instrument.

Intermediate Grinding

The pieces from the breaking process are mixed with a vehicle such as cyclomethicone (preferably D5 and/or D6 cyclomethicone) in a 60:40 ratio of cyclics to antiperspirant glass pieces. The mixture is processed with a Ross homogenizer with a mixing speed of 1000–10,000 rotations per minute (rpm). This processing further breaks the pieces down to about 200 microns whereby a suspension is formed (still in the cyclomethicone vehicle).

Fine Grinding

The suspension from the intermediate grinding is further processed by subjecting the suspension (comprising 40% solid (w/w) with about 800 g of the anhydrous salt powder in 1200 gm of cyclomethicone (D5), and stirring the slurry to make a uniform suspension). The salt suspension is processed on the LabStar I Zeta mill (NETZSCH Inc., Exton, Pa.). The Zeta mill has silicon carbide wetted parts (shaft and chamber) with a screen size of 0.2 mm, and is loaded with a 90% charge of 0.4 mm YTZ (Yttrium coated $ZrO_2$ beads) as grinding media about 1.5 kg). The salt suspension is re-circulated at an average rate of 0.75 kg/min, and the agitator speed is maintained around 3000 RPM. The temperature of the suspension is controlled to stay below 60° C. by passing chilled water (4° C.) at a flow rate of 1/min in a jacket around the vessel. The particle size distribution of the dispersed salt powder is measured with LA-900 Laser Scattering Particle Size Distribution Analyzer (Horiba Instruments, Inc. Irvine, Calif.) every 30 minutes. The ground sample is also collected to analyze the molecular weight distribution of the metal polymers by SEC (Size Exclusion Chromatography) as described in Example 1S.

Example 2P

The processes as described in Method #1 and Method #2 of Example 1P may be repeated with the following changes. The shaft is polyurethane, the bead size used in 0.2 mm, the screen size used is 0.1 mm with more open surface area, and the agitator speed is about 3200 RPM.

Salt Examples

Example 1S: General Analytical Technique

SEC (Size Exclusion Chromatography) analysis is the primary technique used in this invention for characterizing ZAG salts in terms of separating, detecting and measuring zirconium and aluminum polymer species. The chromatogram is run using the following parameters: Waters® 600 analytical pump and controller, Rheodyne® 7725I injector, Protein-Pak® 125 (Waters) column, Waters 996 Photodiode Array Detector at a wavelength of 240 mn, 5.56 mM nitric acid mobile phase, 0.70 ml/min flow rate, 2.0 microliter injection volume. Data was analyzed using Waters® millenium 2.1 software (Waters Corporation, Milford, Mass.). At least five distinguished peaks can be shown for a ZAG sample, each identified by a distribution coefficient (Kd) as follows: Peak 1 (Kd=0), Peak 2 (Kd=0.05), Peak 3 (Kd=0.20), Peak 4 (Kd=0.33) and Peak 5 (or Peak 5 & 6) (Kd=0.53), which is defined by the equation:

$Kd=(Ve-Vo)/(Vt-Vo)$

Where

Ve=elution volume of peak

Vo=exclusion volume of column

Vt=total volume of column

For SEC analysis of a sample of ground salt suspension as made by the method described in Example 1P, the non-aqueous liquid vehicle is removed by means of centrifugation (3900 RPM), the salt is then dissolved in distilled water to make a 10% (w/w) solution, and the solution is used for injection onto the column.

The increase in smaller aluminum species is calculated by obtaining the values for $$\frac{\text{Peak 4 area} + \text{Peak 5 area}}{\text{Peak 3 area} + \text{Peak 4 area} + \text{Peak 5 area}} \text{ before grinding} = P_{before}$$

$$\frac{\text{Peak 4 area}' + \text{Peak 5 area}'}{\text{Peak 3 area}' + \text{Peak 4 area}' + \text{Peak 5 area}'} \text{ after grinding} = P_{after}$$

$(P_{after} - P_{before}) \times 100 \times \%$ increase where the values marked "'" are those taken after grinding.

The decrease in larger zirconium species is obtained by calculating the decrease in the area of Peak 1 as $$\frac{\text{Peak 1 area before grinding} - \text{Peak 1 area after grinding}}{\text{Peak 1 area before grinding}} \times 100 = \% \text{ decrease}$$

using the same SEC technique as described above.

The method described in Example 1P or 2P may be used to obtain the following salts with the method of Example 1S being used to evaluate the increase in the smaller aluminum species the decrease in the larger zirconium species.

Example 2S

Method #1 of Example 1P and the method of Example 2P were used to obtain an enhanced salt as evaluated by the method of Example 1S. A sample of Chlorhydrol Powder (25% in D5 cyclomethicone obtained from Reheis Inc., Berkeley Heights, N.J.) was processed according to the method described in those Example wherein the final grinding step was performed for 90 minutes with the following results ($\mu$.=microns). The SEC method described in Example 1S was performed.

TABLE 1

SEC Analysis for Ground Chlorhydrol Powder

| Status | Peak 2 | Peak 3 | Peak 4 | Peak 5 |
|---|---|---|---|---|
| Parent salt | 26.4% | 41.3% | 10.5% | 21.8% |
| After forming glass | 40.8% | 36.1% | 6.3% | 16.8% |
| After 90 min. grinding | 12.2% | 52.1% | 19.4% | 16.4% |

After grinding for 90 minutes, the mean particle size was 10 microns.

The increase in the amount of smaller aluminum species can be calculated as follows:

(1) proportion of medium and small aluminum species in relation to all aluminum species in parent salt is:

[(41.3+10.5+21.8)/(26.4+41.3+10.5+21.8)]×100=73.6%

(2) proportion of medium and small aluminum species in relation to all aluminum species in salt after grinding is:

[(52.1+19.4+16.4)/(12.2+52.1+19.4+16.4)]×100=87.8%

(3) increase in amount of medium and small aluminum species is:

87.8%−73.6%=14.2%

Example 3S

Method #1 of Example 1P and the method of Example 2P were used to obtain an enhanced salt as evaluated by the method of Example 1S. A sample made from Reach AZP-908 (from Reheis Inc.) 25% AZP 908 glass in D5 cyclomethicone was ground for 90 minutes using the methods described in the Examples with the following results:

TABLE 2

SEC analysis for ground AZP-908 (Peak area distribution)

| Status | Peak 1 | Peak 3 | Peak 4 | Peak 5 |
|---|---|---|---|---|
| Parent salt | 15.7% | 48.5% | 10.6% | 25.1% |
| After forming glass | 21.3% | 41.9% | 6.1% | 30.7% |
| After grinding 90 min. | 0.4% | 42.3% | 28.5% | 28.8% |

After grinding for 90 minutes, the mean particle size was 10 microns.

The increase in the amount of smaller aluminum species can be calculated as follows:

(1) proportion of small aluminum species in relation to all aluminum species in the parent salt is:

[(10.6+25.1)/(48.5+10.6+25.1)]×100=42.3%

(2) proportion of small aluminum species in relation to all aluminum species in the salt after grinding is:

[(28.5+28.8)/(42.3+28.5+28.8)]×100=57.5%

(3) increase in the amount of medium and small aluminum species is:

57.5%−42.3%=15.2%

The increase in the amount of medium and smaller zirconium species can be calculated as follows:

(1) area for Peak 1 (Parent salt)=15.7−area for Peak 1 after grinding=0.4

(2) 15.7−0.4=15.3

(3) [15.7/15.3]×100=97% reduction in large zirconium species.

Example 4S

Method #2 of Example 1P and the method of Example 2P were used to obtain an enhanced salt as evaluated by the method of Example 1S. A glass sample was formed by mixing 50% Chlorhydrol powder, 6% ammonium acetate, and 44% distilled water. The glass was formed into an initial powder by the intermediate grinding method described in Example 1P. The initial powder was then suspended in D5 cyclomethicone in a concentration of 25% and fine grinding was done for 90 minutes using the method described in Example 1P with the following results:

TABLE 3

SEC Analysis for Ground Chlorhydrol

| Status | Peak 1 | Peak 3 | Peak 4 | Peak 5 |
|---|---|---|---|---|
| Parent salt | 26.4% | 41.3% | 10.5% | 21.8% |
| After forming glass | 44.3% | 29.3% | 4.3% | 22.1% |
| After grinding 90 min. | 16.6% | 33.5% | 12.2% | 37.7% |

After grinding for 90 minutes, the mean particle size was 11 microns.

In this Example the amount of small and medium Al species was increased from 73.6–83.4%

Formulation Examples

The following formulations can be made with enhanced salts of lower refractive index made according to his invention using the method and salts described above. A particular enhanced salt of interest is the one described in Example 2S which may be described as a ground active antiperspirant made with a 25% suspension of chlorhydrol glass in cyclcomethicone. The average particle size of this enhanced salt should be targeted to be in the range of 5–20 microns with at least 50% of the particles being 10 microns. All amounts are in percent by weight based on the entire weight of the composition. The enhanced salt is prepared by the wet grinding method of the invention.

Example #1F—Roll-On

A roll-on product may be made by combining the following ingredients with mixing until homogeneous:

| | |
|---|---|
| Enhanced salt (25% active/cyclomethicone) | 99% |
| Fragrance | 1% |

Example #2F—Soft Solid Without Elastomer

A soft solid product may be made by combining the following ingredients with mixing until homogeneous:

| | |
|---|---|
| Enhanced Salt (25%) | 93.4% |
| Degussa R-812 Hydrophobically Modified Silica | 3.6% |
| Fragrance | 1.0% |

Examples #3F—5F—Soft Solid With Elastomer

Soft solid products may be made by combining the following ingredients with mixing until homogeneous. Note that three formulations (3F, 4F, and 5F) are given.

| Ingredient | 3F | 4F | 5F |
|---|---|---|---|
| Enhanced Salt (25%) | 66.0 | 50 | 33.0 |
| Shin Etsu KSG-15 Elastomer (Shin Etsu Silicones of America, Akron, Ohio) | 25 | 36.5 | 50.0 |
| AZZ 902 Al-Zirconium trichlorohydrex | 8.0 | 12.5 | 16.0 |
| Fragrance | 1.0 | 1.0 | 1.0 |

Example #6F—Low White Residue Antiperspirant Stick

A soft solid or stick product (low white residue as compared to a product such as Lady Speed Stick by Mennen) may be made by combining the following ingredients with mixing until homogeneous:

| | |
|---|---|
| Enhanced Salt (25%) | 58.7% |
| Stearyl Alcohol | 17.4% |
| PPG-14 Butyl Ether | 11.9% |
| Phenyl trimethicone | 5.0% |
| Hydrogenated Castor Oil | 4.0% |
| PEG-8 distearate | 2.0% |
| Fragrance | 1.0% |

Also, a mixed system may be used with regular salt and enhanced salt so that 52.2% of the enhanced salt (25% in cyclomethicone)+6.5% of an aluminum zirconium tetrachlorohydrex salt may be used.

Example #7F: Anhydrous Roll-On Antiperspirant

A roll-on product may be made by combining the following ingredients with mixing until homogeneous:
80.00% of a 25% suspension of an enhanced salt as described in any of the "S" Examples
9.00% C12–15 alkyl benzoate (Finsolv TN from Finetex, Inc., Elmwood Park, N.J.)
10.50% cyclomethicone (D5)
0.50% fragrance

Example #8F: Roll-On Antiperspirant (Suspension)

A roll-on suspension product may be made by combining the following ingredients with mixing until homogeneous:
24.00% cyclomethicone (D5)
1.40% of an aluminum zirconium trichlorohydrex gly antiperspirant salt
71.4% of a 25% suspension of an enhanced salt as described in any of the "S" Examples
3.00% quaternium-18 hectorite
1.00% propylene carbonate
0.50% fragrance
0.10% fumed silica Also, a mixed system may be used with regular salt and enhanced salt so that 70.0% of the enhanced salt (25% in cyclomethicone)+1.40% of an aluminum zirconium trichlorohydrex salt may be used.

Example #9F: Antiperspirant Stick

A stick product may be made by combining the following ingredients with mixing, heating until all the waxes are solubilized, and until the whole mixture is homogeneous. The product is then poured into appropriate packages.
68.00% of a 25% suspension of an enhanced salt as described in any of the "S" Examples
14.00% stearyl alcohol
5.00% hydrogenated castor oil
0.50% fumed silica
0.50% fragrance
5.00% C12–15 alkyl benzoate
7.00% cyclomethicone (D5)

Also, a mixed system may be used with regular salt and enhanced salt so that 60.0% of the enhanced salt (25% in cyclomethicone)+8.00% of an aluminum zirconium trichlorohydrex salt may be used.

Example #10F: Antiperspirant Stick

A stick product may be made by combining the following ingredients with mixing, heating until all the waxes are solubilized, and until the whole mixture is homogeneous. The product is then poured into appropriate packages.
2.50% cyclomethicone (D5)
68.00% of a 25% suspension of an enhanced salt as described in any of the "S" Examples
3.00% PEG-8 distearate
8.00% hydrogenated castor oil
18.00% stearyl alcohol
0.50% fragrance Also, a mixed system may be used with regular salt and enhanced salt so that 60.0% of the enhanced salt (25% in cyclomethicone)+8.00% of an aluminum zirconium trichlorohydrex salt may be used.

Example #11F: Wax Based Antiperspirant Cream

A cream product may be made by combining the following ingredients with mixing until homogeneous. No heating is required.
5.00% cyclomethicone (D5)
15.00% dimethicone (50 centistokes)
68.00% of a 25% suspension of an enhanced salt as described in any of the "S" Examples
6.50% hydrogenated castor oil
5.00% alkyl silicone wax (stearoxytrimethyl siloxane)
0.50% fragrance Also, a mixed system may be used with regular salt and enhanced salt so that 60.0% of the enhanced salt (25% in cyclomethicone)+8.00% of an aluminum zirconium trichlorohydrex salt may be used.

Example #12F: Silicone Based Soft Solid Antiperspirant

A soft solid product may be made by combining the following ingredients with mixing until homogeneous:
70.00% of a 25% suspension of an enhanced salt as made by any of the "S" Examples described above
24.50% cyclomethicone and dimethicone crosspolymer (KSG-15 from Shin-Etsu)
5.00% C12–15 alkyl benzoate
0.50 fragrance

Example #13F: Wax Based Soft Solid Antiperspirant

A soft solid product may be made by combining the following ingredients with mixing until homogeneous:
60.00% of a 25% suspension of an enhanced salt as made by any of the "S" Examples described above
15.00% hexanediol behenyl beeswax
15.00% phenyl trimethicone
9.5% dimethicone (up to 350 centistokes, especially 200–350 cst)
0.50% fragrance Also, a mixed system may be used with regular salt and enhanced salt so that 60.0% of the enhanced salt (25% in cyclomethicone)+10.00% of an aluminum zirconium trichlorohydrex salt may be used.

Example #15F: Soft Solid Antiperspirant

A soft solid product may be made by combining the following ingredients with mixing until homogeneous:
25% of an enhanced salt as made by any of the "S" Examples described above
46% cyclomethicone (D5)
10.0% isocetyl alcohol
1% fragrance
5.0% quaternium-18 hectorite
13% starch (DRY FLO corn starch from National Starch, Findeme, N.J.)

Example #16F: Roll-On Antiperspirant

A roll-on product may be made by combining the following ingredients with mixing until homogeneous:
25% of an enhanced salt as made by any of the "S" Examples described above
66% cyclomethicone (D5)
5.0% dimethicone (200 centistokes)
3.0% quaternium-18 hectorite
1% fragrance

Example #17F: Aerosol Antiperspirant

An aerosol product may be made by combining the following ingredients with mixing until homogeneous:
20% of an enhanced salt as made by any of the "S" Examples described above
10% cyclomethicone (D5)
2% dimethicone (10 centistokes)
2% quaternium-18 hectorite
1% fragrance
65% propellant

Example #18F: Clear/Translucent Stick

A clear/translucent stick may be made by combining the following ingredients with mixing until homogeneous:
60% of an enhanced salt (25% salt in D5 cyclomethicone) as made by any of the "S" Examples described above
10% polyamide gellant of Formula IIIA where DP=15
24% PPG-3-myristyl ether
5% phenyl trimethicone (DC 556 from Dow Corning)
1% fragrance.

We claim:

1. A method for forming micronized antiperspirant salts comprising aluminum or aluminum and zirconium, wherein the refractive index for the micronized antiperspirant salts is in the range of 1.42–1.49 for aluminum salts and 1.46–1.52 for Al—Zr salts, and wherein the method comprises the steps of:
   (1) forming an aqueous salt solution of a parent salt and solvent wherein the parent salt is selected from the group consisting of aluminum salts and aluminum zirconium salts and the glycol content of the salt solution is less than 5 weight %;
   (2) pouring the salt solution onto a bounded flat surface;
   (3) evaporating the solvent from the salt solution so as to form a glass;
   (4) breaking up the glass using one or more steps to form particles having an average size in the range of 0.5–2.00 cm$^2$;
   (5) mixing the particles from step (4) with a non-aqueous liquid vehicle in which the salt is not appreciably soluble and subjecting the mixture to a homogenizing process to form a suspension with particles having an average size of less than or equal to 200 microns; and
   (6) grinding the mixture from step (5) at a temperature in the range of 20–70 degrees C. without added water or external heating being required so that the particles in the suspension have an average particle size of less than or equal to 20 microns.

2. The method as claimed in claim 1 wherein external heat is applied to form the salt solution.

3. The method as claimed in claim 1 wherein a promoter is added to the salt solution to accelerate glass formation.

4. The method as claimed in claim 1 wherein the parent salt is selected from the group consisting of aluminum chlorides, zirconyl hydroxychlorides, zirconyl oxychlorides, basic aluminum chlorides, basic aluminum chlorides combined with zirconyl oxychlorides and hydroxychlorides, and organic complexes of each of basic aluminum chlorides with or without zirconyl oxychlorides and hydroxychlorides and mixtures of any of the foregoing.

5. The method as claimed in claim 4 wherein the parent salt is selected from the group consisting of aluminum chlorohydrate, aluminum chloride, aluminum sesquichlorohydrate, aluminum chlorohydrol-propylene glycol complex, zirconyl hydroxychloride, aluminum-zirconium glycine complex, aluminum dichlorohydrate, aluminum chlorohydrex in propylene glycol, aluminum chlorohydrex in polyethylene glycol, aluminum dichlorohydrex in propylene glycol, aluminum dichlorohydrex in polyethylene glycol, aluminum zirconium trichlorohydrex gly propylene glycol complex, aluminum zirconium trichlorohydrex gly dipropylene glycol complex, aluminum zirconium tetrachlorohydrex gly propylene glycol complex, aluminum zirconium tetrachlorohydrex gly dipropylene glycol complex, and mixtures of any of the foregoing, provided that the amount of glycol in the salt solution is maintained at less than 5 weight %.

6. The method as claimed in claim 4 wherein the parent salt is selected from the group consisting of aluminum chlorohydrate, aluminum dichlorohyrate, aluminum sesquichlorohydrate, aluminum zirconium trichlorohyrate, aluminum zirconium tetrachlorohydrate, aluminum zirconium pentachlorohydrate, aluminum zirconium octachlorohydrate, aluminum zirconium trichlorohydrex gly, aluminum zirconium tetrachlorohydrex gly, aluminum zirconium pentachlorohydrex gly, and mixtures of any of the foregoing, provided that the amount of glycol in the salt solution is maintained at less than 5 weight %.

7. The method as claimed in claim 4 wherein the parent salt is selected from the group consisting of aluminum chlorohydrate, aluminum chloride, aluminum sesquichlorohydrate, zirconyl hydroxychloride, aluminum-zirconium glycine complex, aluminum chlorohydrex in propylene glycol, aluminum chlorohydrex in polyethylene glycol, aluminum dichlorohydrex in propylene glycol, aluminum dichlorohydrex in polyethylene glycol, and mixtures of any of the foregoing, provided that the amount of glycol in the salt solution is maintained at less than 5 weight %.

8. The method as claimed in claim 4 wherein the parent salt is selected from the group consisting of aluminum zirconium trichlorohydrex and aluminum zirconium tetrachlorohydrex either with or without glycine.

9. The method as claimed in claim 4 wherein the parent salt is selected from the group consisting of enhanced efficacy aluminum salts and enhanced efficacy aluminum/zirconium salt-glycine materials, having enhanced efficacy due to improved molecular distribution of Al and/or Zr species.

10. The method as claimed in claim 4 wherein the parent salt is selected from the group consisting of aluminum chlorohydrate, aluminum zirconium tetrachlorohydrex, aluminum zirconium trichlorohydrex, aluminum zirconium octachlorohydrex, and aluminum zirconium pentachlorohydrex.

11. The method as claimed in claim 1 wherein the solvent is water.

12. The method as claimed in claim 1 wherein the solvent comprises less than 5% by weight based on the weight of the solution of ethanol, propanol, isopropanol, glycols, polyglycols, dimethylisosorbide, sorbitol, glycerine, or mixtures of any combination of the foregoing.

13. The method as claimed in claim 1 wherein the promoter is selected from the group consisting of borax, sodium phosphates, sodium tetraborate, C2–C3 monocarboxylic acids (and sodium and ammonium salts thereof), C2–C5 dicarboxylic acids (and sodium and ammonium salts thereof), citric acid and aspartic acid, C2–C10 carboxylates, and sodium tetraborate and is used in an amount of 4–10 weight % based on the total weight of the solution of antiperspirant salt.

14. The method as claimed in claim 13 wherein the promoter is selected from the group consisting of acetic acid, propionic acid, lactic acid, adipic acid, glutaric acid, maleic acid, diglycolic acid, oxalic acid, succinic acid, malonic acid, citric acid, aspartic acid, sodium acetate, ammonium acetate, ammonium formate, sodium propionate, sodium lactate, sodium succincate, sodium fumarate, sodium maleate, and ammonium citrate.

15. The method as claimed in claim 13 wherein the promoter is used in a solution having a concentration of salt in the range of 50–60%.

16. The method as claimed in claim 1 wherein the non-aqueous liquid vehicle is selected from the group consisting of:
  (a) cosmetic esters;
  (b) glycols;
  (c) volatile silicones;
  (d) non-volatile silicones;
  (e) hydrocarbons;
  (f) alcohols having more than three carbons; and
  (g) mixtures of the foregoing.

17. The method as claimed in claim 16 wherein the non-aqueous liquid vehicle is selected from the group consisting of:
  (a) cosmetic esters selected from the group consisting of C6–C22 straight or branched chained ethoxylates, propoxylates, benzoates, and adipates;
  (b) glycols and polyols selected from the group consisting of propylene glycol and dipropylene glycol;
  (c) volatile silicones selected from the group consisting of D4, D5, D6 cyclomethicones and mixtures of any of the foregoing;
  (d) non-volatile silicones selected from polydimethicones having a viscosity of up to 350 centistokes;
  (e) mineral oils;
  (i) alcohols having more than three carbons; and
  (g) mixtures of any of the foregoing.

18. The method as claimed in claim 16 wherein the non-aqueous liquid vehicle is selected from the group consisting of one or more of D4, D5, or D6 cyclomethicones, that may optionally contain a minor amount of less than 5 weight % of one or more of water, mineral oils, glycols and polyols, and low viscosity fatty esters having 8–18 carbons, provided that the active is in a suspension with no more than 5 weight % of the salt dissolved therein.

19. An antiperspirant and/or deodorant composition comprising an effective amount of a micronized antiperspirant salt made according to the method of claim 1, provided the composition is:

(a) anhydrous with <5% water;

(b) does not contain methanol, ethanol or isopropanol in an amount greater than 5%; and (c) formulated so that the total amount of glycol component does not exceed 50% by weight of the amount of micronized antiperspirant salt.

20. An antiperspirant and/or deodorant composition according to claim 19 further comprising a gelling agent selected from the group consisting of C10–40 linear alcohols; paraffins having a melting point in the range of 54–90 degrees C.; dibutyl lauryl glutamide; 12-hydroxy stearic acid; Japan wax; dibenzylidene sorbitol; polyethylenes having a molecular weight in the range of 200–5,000, with a melting temperature in the range of 50–150 degrees C. and a polydispersity in the range of 1–10; and polyamides which are multiples of a unit represented by Formula A:

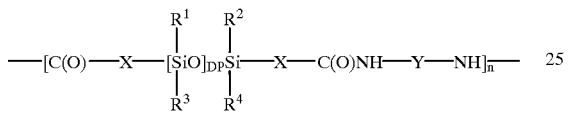

Formula A where:

(1) DP is selected from the group consisting of 1–700, (2) n is a number selected from the group consisting of 1–500, (3) X is a linear or branched chain alkylene having 1–30 carbons, (4) Y is selected from the group consisting of linear or branched chain alkylenes having 1–40 carbons, wherein (a) the alkylene group may optionally and additionally contain in the alkylene portion at least one of (i) 1–3 amide linkages; (ii) C5 or C6 cycloalkane; and (iii) phenylene optionally substituted by 1–3 members selected independently from the group consisting of C1–C3 alkyls; and (b) the alkylene group itself may optionally be substituted by at least one member selected from the group consisting of (i) hydroxy; (ii) C3–C8 cycloalkane; (iii) 1–3 members selected independently from the group consisting of C1–C3 alkyls; phenyl optionally substituted by 1–3 members selected independently from the group consisting of C1–C3 alkyls; (iv) C1–C3 alkyl hydroxy; and (v) C1–C6 alkyl amine; or Y=Z where Z=T($R^{20}$)($R^{21}$)($R^{22}$) where each of $R^{20}$, $R^{21}$ and $R^{22}$ are independently selected from the group consisting of linear and branched C1–C10 alkylenes; and T is selected from the group consisting of CR, where R is selected from hydrogen, the group consisting of the group defined for $R^1$–$R^4$, and a trivalent atom selected from N, P and Al;

(5) each of $R^1$–$R^4$ is independently selected from the group consisting of methyl, ethyl, propyl, isopropyl, a siloxane chain, and phenyl, wherein the phenyl may optionally be substituted by 1–3 members from the group consisting of methyl and ethyl;

(6) the values for X, Y, DP, and $R^1$–$R^4$ may be the same or different for each unit of the polyamide.

21. An antiperspirant and/or deodorant composition as claimed in claim 20 wherein the polyamide is a multiple of a unit represented by Formula IIIA:

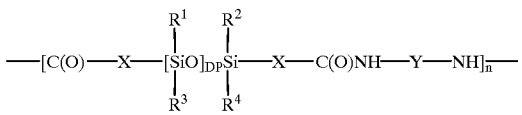

Formula IIIA where:

(1) DP is a number in the range of 5–30;

(2) n is a number selected from the group consisting of 1–500;

(3) X is a linear or branched chain alkylene having 1–30 carbons;

(4) Y is selected from the group consisting of linear and branched chain alkylenes having 1–40 carbons, wherein (a) the alkylene group may optionally and additionally contain in the alkylene portion at least one of the members of a group consisting of (i) 1–3 amide linkages; (ii) C5 or C6 cycloalkane (as a cycloalkylene linkage); and (iii) phenylene optionally substituted by 1–3 members selected independently from the group consisting of C1–C3 alkyls; and (b) the alkylene group itself may optionally be substituted by at least one member selected from the group consisting of (i) hydroxy; (ii) C3–C8 cycloalkane; (iii) 1–3 members selected independently from the group consisting of C1–C3 alkyls; phenyl optionally substituted by 1–3 members selected independently from the group consisting of C1–C3 alkyls; (iv) C1–C3 alkyl hydroxy; and (v) C1–C6 alkyl amine; or $$Z^2 = R^{20}\!\!-\!\!T\!\!-\!\!R^{21}\!\!-\!\!$$
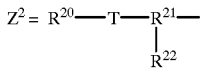

wherein each of $R^{20}$, $R^{21}$ are independently selected from the group consisting of linear and branched C1–C10 alkylenes; $R^{22}$ is selected from the group consisting of linear and branched C1–C10 alkanes; and T is selected from the group consisting of (1) a trivalent atom selected from N, P and Al; and (2) —CR, where R is selected from the group consisting of hydrogen, methyl, ethyl, propyl, isopropyl, a siloxane chain, and phenyl, wherein the phenyl may optionally be substituted by 1–3 members from the group consisting of methyl and ethyl, especially methyl and ethyl and most especially methyl; and (5) each of $R^1$–$R^4$ is independently selected from the group consisting of methyl, ethyl, propyl, isopropyl, a siloxane chain, and phenyl, wherein the phenyl may optionally be substituted by 1–3 members from the group consisting of methyl and ethyl.

22. An antiperspirant and/or deodorant composition according to claim 21 comprising a polyamide of Formula IIIA wherein the DP is in the range of 12–18 and each of $R^1$–$R^4$ is methyl, and wherein the composition is formulated to be clear.

23. An antiperspirant and/or deodorant composition according to claim 22 wherein the composition comprises at least 8 weight % of a polyamide of Formula IIIA where the DP is 5.

24. An antiperspirant and/or deodorant composition according to claim 21 wherein for the polyamides of Formula IIA, $R^1$–$R^4$ are each methyl and the polyamide of Formula IIIA is selected from the group consisting of:

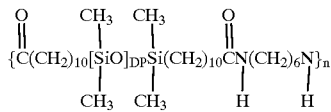

a) polyamides of Formula IIIA where the DP is in the range of 5–30;
b) polyamides of Formula IIIB:

Formula IIIB

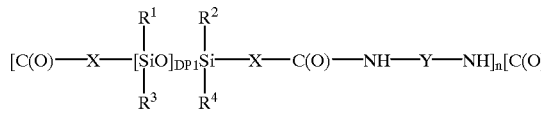

where DP is from 5–30 and n has the same value as in Formula IIIA;
c) polyamides of Formula IIIB wherein the DP is from 5–20;
d) polyamides of Formula IIIB wherein the DP is from 12–18;
e) polyamides of Formula IIIB wherein the DP is 15;
f) polyamides of Formula IIIA where the values of X, Y, DP and $R^1$–$R^4$ remain the same in each unit of the polymer;
g) polyamides of Formula IIIB where the value of DP and n remain the same for each unit of the polymer;
h) Polyamides of Formula IIIA containing multiple siloxane block lengths as shown in Formula IIIC:

Formula IIIC

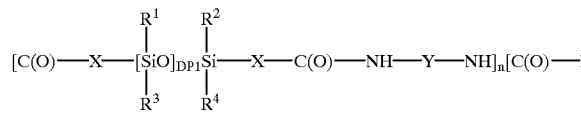

where X, Y, n, and $R^1$–$R^4$ have the meanings described above for Formula IIIA; m is selected from the same groups as defined for n, and n and mn denote the total number of units enclosed within the brackets, with the individual units arranged with regular, alternating, block or random sequencing; $R^5$–$R^8$ is selected from the same group as defined for $R^1$–$R^4$; DP1 and DP2 may be the same or different and are each independently selected from the same group as defined for DP; and the units denominated by n and m may be structured to form either block (regularly sequenced) or random copolymers.

i) polyamides of Formula A containing siloxane block lengths of Formula IIIC wherein all of the R groups are selected to be methyl.
j) polyamides of Formula IIIA containing siloxane block lengths of Formula IIIC wherein DP1=DP2.
k) polyamides of Formula IIIA containing siloxane block lengths of Formula IIIC wherein all of the R groups are selected to be methyl and DP1DP2.
l) Polyamides synthesized from multiple diamines as shown in Formula IIID:

Formula IIID

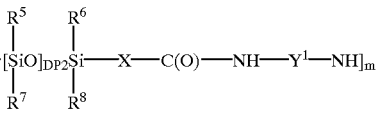

where X, Y, m, n, and $R^1R^8$, DP1, DP2 have the same meanings as described above for Formula IIIA and Formula IIIC; $Y^1$ is independently selected from the same group as defined for Y; and the units denominated by n and m may be structured to form either block (regularly sequenced) or random copolymers.

m) polyamides of Formula IIID where DP1=DP2.
n) polyamides of Formula IIID where all of the R groups are selected to be methyl. Polyamides of Formula IIID where all of the R groups are selected to be methyl and DP1=DP2.

25. An antiperspirant and/or deodorant composition according to claim 21 which is a clear stick comprising:
(a) 0.5–50% of a micronized antiperspirant salt made according to claim 1;
(b) 20–80% cyclomethicone;
(c) 0–50% emollients; and
(d) 10–15% of a polyamide of Formula IIIA with a DP=15.

26. An antiperspirant and/or deodorant composition according to claim 21 which is a translucent or opaque stick comprising:
(a) 0.5–50% of a micronized antiperspirant salt made according to claim 1;
(b) 20–80% cyclomethicone;
(c) 0–50% emollients;
(d) 4–10% of 10–15% of a gellant selected from the group consisting of a polyamide of Formula IIIA or an elastomer, or a mixture thereof; and
(e) 0–3% fragrance.

27. An antiperspirant and/or deodorant composition according to claim 21 which is a clear soft solid comprising:
(a) 0.5–50% of a micronized antiperspirant salt made according to claim 1;
(b) 20–80% cyclomethicone;
(c) 0–50% emollients;

(d) 4–10% of 10–15% of a gellant selected from the group consisting of a polyamide of Formula IIIA or an elastomer, or a mixture thereof; and (e) 0–3% fragrance.

28. An antiperspirant and/or deodorant composition according to claim 21 which is a translucent or opaque soft solid comprising:

(a) 0.5–50% of a micronized antiperspirant salt made according to claim 1;

(b) 20–80% cyclomethicone;

(c) 0–50% emollients;

(d) 4–10% of 10–15% of a gellant selected from the group consisting of C10–40 linear alcohols; paraffins having a melting point in the range of 54–90 degrees C.; dibutyl lauryl glutamide; 12-hydroxy stearic acid; Japan wax; dibenzylidene sorbitol; polyethylenes having a molecular weight in the range of 200–5,000, with a melting temperature in the range of 50–150 degrees C. and a polydispersity in the range of 1–10 or a mixture thereof; and (e) 0–3% fragrance.

29. An antiperspirant and/or deodorant composition according to claim 19 which is a clear, translucent or opaque roll-on comprising:

(a) 20–90% cyclomethicone;

(b) 0–20% dimethicone having a viscosity $\leq 350$ centistokes;

(c) 0.5–50% a micronized antiperspirant active slat according to claim 1; and (d) 0–3% fragrance.

30. An antiperspirant and/or deodorant composition according to claim 19 which is an aerosol comprising:

(a) 5–30% cyclomethicone;

(b) 50–80% propellant;

(c) 0–20% dimethicone haven't a viscosity $\leq 350$ centistokes;

(d) 0.5–50% a micronized antiperspirant active slat according to claim 1;

(e) 0–3% fragrance; and (f) 0–10% quaternium-18 hectorite.

31. An antiperspirant and/or deodorant composition according to claim 19 which is a pump spray comprising:

(a) 5–30% cyclomethicone;

(b) 0–20% dimethicone having a viscosity $\leq 350$ centistokes;

(c) 0.5–50% a micronized antiperspirant active slat according to claim 1;

(d) 0–3% fragrance; and (e) 0–10% quaternium-18 hectorite.

32. A method for forming micronized antiperspirant salts comprising tin or titanium salts used alone or in combination with aluminum compounds wherein the refractive index for the micronized antiperspirant salts is in the range of 1.42–1.55, and wherein the method comprises the steps of:

(1) forming an aqueous salt solution of a parent salt and solvent wherein the glycol content of the salt solution is less than 5 weight %;

(2) pouring the salt solution onto a bounded flat surface;

(3) evaporating the solvent from the salt solution so as to form a glass;

(4) breaking up the glass using one or more steps to from particles having an average size in the range of 0.5–2.00 cm$^2$;

(5) mixing the particles from step (4) with a non-aqueous liquid vehicle in which the salt is not appreciably soluble and subjecting the mixture to an intermediate grinding process to form a suspension with particles having an average size of less than 200 microns; and (6) grinding the mixture from step (5) at a temperature in the range of 20–70 degrees C. without added water or external heating being required so that the particles in the suspension have an average particle size of less than or equal to 20 microns.

33. The method as claimed in claim 32 wherein external heat is applied to form the salt solution.

34. The method as claimed in claim 32 wherein a promoter is added to the salt solution to accelerate glass formation.

* * * * *